United States Patent
Hatsuda et al.

(10) Patent No.: US 7,183,456 B2
(45) Date of Patent: Feb. 27, 2007

(54) WATER-ABSORBENT RESIN AND PRODUCTION PROCESS THEREFOR

(75) Inventors: Takumi Hatsuda, Takasago (JP); Yoshio Irie, Himeji (JP); Masatoshi Nakamura, Himeji (JP); Katsuyuki Wada, Himeji (JP); Shinichi Fujino, Himeji (JP); Kazuki Kimura, Himeji (JP); Kunihiko Ishizaki, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 310 days.

(21) Appl. No.: 10/764,535

(22) Filed: Jan. 27, 2004

(65) Prior Publication Data

US 2004/0186244 A1    Sep. 23, 2004

Related U.S. Application Data

(62) Division of application No. 09/945,812, filed on Sep. 5, 2001, now Pat. No. 6,720,389.

(30) Foreign Application Priority Data

Sep. 20, 2000  (JP) .............................. 2000-285658
Nov. 6, 2000   (JP) .............................. 2000-336813

(51) Int. Cl.
A61F 13/15    (2006.01)
B32B 5/16     (2006.01)
C08F 8/00     (2006.01)

(52) U.S. Cl. .................... 604/372; 604/367; 604/358; 428/402; 525/384

(58) Field of Classification Search ..................... None
See application file for complete search history.

(56) References Cited

U.S. PATENT DOCUMENTS

| | | | |
|---|---|---|---|
| 3,661,815 A | 5/1972 | Smith | 260/17.4 |
| 4,076,663 A | 2/1978 | Masuda et al. | 260/17.4 |
| 4,541,871 A | 9/1985 | Obayashi et al. | 106/197.2 |
| 4,666,983 A | 5/1987 | Tsubakimoto et al. | 525/119 |
| 4,734,478 A | 3/1988 | Tsubakimoto et al. | 527/300 |
| 5,147,343 A | 9/1992 | Kellenberger | 604/368 |
| 5,369,148 A | 11/1994 | Takahashi et al. | 523/315 |
| 5,422,405 A | 6/1995 | Dairoku et al. | 525/384 |
| 5,486,569 A | 1/1996 | Henderson et al. | |
| 5,597,873 A | 1/1997 | Chambers et al. | 525/330.1 |
| 5,601,542 A | 2/1997 | Melius et al. | 604/368 |
| 5,760,080 A | 6/1998 | Wada et al. | 524/559 |
| 6,071,976 A | 6/2000 | Dairoku et al. | 521/50 |
| 6,127,454 A | 10/2000 | Wada et al. | 523/200 |
| 6,184,433 B1 | 2/2001 | Harada et al. | 604/372 |
| 6,254,990 B1 * | 7/2001 | Ishizaki et al. | 428/402 |
| 6,323,252 B1 | 11/2001 | Gartner et al. | |
| 6,576,713 B2 | 6/2003 | Ishizaki et al. | |
| 6,599,989 B2 | 7/2003 | Wada et al. | |
| 6,964,998 B2 | 11/2005 | Wada et al. | |
| 2005/0272600 A1 | 12/2005 | Wada et al. | |

FOREIGN PATENT DOCUMENTS

| | | |
|---|---|---|
| CN | 1041735 C | 1/1999 |
| CN | 1229808 | 9/1999 |
| CN | 2389712 Y | 8/2000 |
| EP | 0532002 | 3/1993 |
| EP | 0 695 763 A1 | 2/1996 |
| EP | 0942014 | 9/1999 |
| EP | 1 130 045 A2 | 9/2001 |
| JP | 466515 | 12/1971 |
| JP | 4943395 | 11/1974 |
| JP | 51125468 | 11/1976 |
| JP | 5214689 | 2/1977 |
| JP | 5315959 | 5/1978 |
| JP | 5584304 | 6/1980 |
| JP | 58180233 | 10/1983 |
| JP | 59189103 | 10/1984 |
| JP | 6018690 | 5/1985 |
| JP | 6116903 | 1/1986 |
| JP | 61101536 | 5/1986 |
| JP | 6148521 | 10/1986 |
| JP | 04246403 | 9/1992 |
| JP | 4246403 | 9/1992 |
| JP | 5200068 | 8/1993 |
| JP | 656931 | 3/1994 |
| JP | 6184320 | 7/1994 |
| JP | 6254118 | 9/1994 |
| JP | 6313043 | 11/1994 |
| JP | 782210 | 3/1995 |
| JP | 9208515 | 8/1997 |

(Continued)

Primary Examiner—Michael J. Feely
(74) Attorney, Agent, or Firm—Roylance, Abrams, Berdo & Goodman, L.L.P.

(57) ABSTRACT

In a production process for a water-absorbent resin, comprising the steps of: blending a liquid material and a water-absorbent resin; and heating the resultant mixture in order to produce a modified water-absorbent resin, the present invention is to provide: a method for uniformly and efficiently treating a water-absorbent resin favorably in view of industry, and as a result, a good-balanced water-absorbent resin having various excellent properties, such absorption capacity without a load, absorption capacity under a load, and single-layer absorption capacity under a load in contact with an aqueous liquid. The production process comprises the step of spray-blending a water-absorbent resin (A) and a liquid material (B) with a blending apparatus equipped with a spray nozzle (C), wherein the liquid material (B) is sprayed from the spray nozzle (C) and its spray pattern is a circular and hollow cone shape or a double-convex-lens and elliptic cone shape. In addition, the production process comprises the step of heat-treating a water-absorbent resin under an atmosphere having a dew point of not higher than 60° C. and a temperature of not lower than 90° C., wherein the water-absorbent resin is obtained after a drying step following a pulverization step.

9 Claims, 4 Drawing Sheets

FOREIGN PATENT DOCUMENTS

| | | |
|---|---|---|
| JP | 9235378 | 9/1997 |
| JP | 10500712 | 1/1998 |
| JP | 10265582 | 10/1998 |
| JP | 1160975 | 3/1999 |
| JP | 2918807 | 4/1999 |
| JP | 2918808 | 4/1999 |
| JP | 11267500 | 10/1999 |
| JP | 11349625 | 12/1999 |
| WO | 9117200 | 11/1991 |
| WO | WO 98/49221 | 11/1998 |

\* cited by examiner

WATER-ABSORBENT RESIN AND PRODUCTION PROCESS THEREFOR

This application is a divisional application of U.S. Ser. No. 09/945,812 (filed Sep. 5, 2001), now U.S. Pat. No. 6,720,389. Both claim foreign priority to Japanese Application Nos. 2000-285658 (filed Sep. 20, 2000) and 2000-336813 (filed Nov. 6, 2000).

BACKGROUND OF THE INVENTION

A. Technical Field

The present invention relates to a water-absorbent resin and a production process therefor. More particularly, the present invention relates to a production process for a modified water-absorbent resin by carrying out a specific step, and a novel water-absorbent resin as surface-crosslinked with a polyhydric alcohol.

B. Background Art

In recent years, water-absorbent resins are widely used as one of materials constituted of sanitary materials, such as disposable diapers, sanitary napkins, and incontinent pads, for the purpose of causing the water-absorbent resins absorb much water. In addition to the sanitary materials, the water-absorbent resins are widely used as dripping sheets for soil water-holding agents and foods, for the purpose of absorbing or retaining water.

As to these water-absorbent resins, the following are known as their examples: hydrolyzed copolymers of starch-acrylonitrile (JP-B43395/1974), neutralized graft polymers of starch-acrylic acid (JP-A-125468/1976), saponified copolymers of vinyl acetate-acrylic acid ester (JP-A-14689/1977), and hydrolyzed copolymers of acrylonitrile or acrylamide (JP-B-15959/1978), or crosslinked polymers of these hydrolyzed copolymers, and partially-neutralized crosslinked poly(acrylic acid) (JP-A-84304/1980).

These water-absorbent resins are generally obtained by polymerizing and drying, and pulverizing and classifying when the occasion demands. However, the above water-absorbent resins are usually modified by further adding various compounds to the resultant water-absorbent resins so that the water-absorbent resins would have additional function after polymerizing and drying.

It is said that the above-mentioned water-absorbent resins should be excellent in the following properties: the absorption capacity, the absorption speed, the liquid permeability, the gel strength of hydrogel, the suction power to suck up water from a base material containing an aqueous liquid, and so on, upon contact with an aqueous liquid such as a body fluid. However, relations between these properties do not necessarily display positive correlations. For example, as the absorption capacity increases, some other properties such as liquid permeability, gel strength, and absorption speed deteriorate. In addition, there are some water-absorbent resins having higher absorption capacity, which form so-called fish eyes in contact with an aqueous liquid, and have extremely low absorption capacity under a load because water is not dispersed in the entirety of the water-absorbent resin particles.

When producing the water-absorbent resins, as to a method for modifying the above-mentioned water-absorption properties of the water-absorbent resin in good balance, namely, as to a method for modifying the water-absorbent resin, an art in which the neighborhood of the surface of the water-absorbent resin is crosslinked, what is called, a surface-crosslinking art is known. Examples of these crosslinking agents as used are polyhydric alcohols, polyglycidyl ethers, haloepoxy compounds, polyaldehydes, polyamines, and polyvalent metal salts.

The most important matter thought in this surface-crosslinking step is to surface-crosslink the surface of water-absorbent resin particles uniformly, and therefore, it is important that the water-absorbent resin before surface-crosslinking is uniformly blended with a surface-crosslinking agent. As to an art in which this water-absorbent resin before surface-crosslinking is uniformly blended with the surface-crosslinking agent, various methods are disclosed until now. For example, the following methods are known: a method which involves the use of crosslinking agents having a different solubility parameter together (JP-A-184320/1994 (corresponding to U.S. Pat. No. 5,422,405)); a method which involves the use of a specific material as the material of the inner surface of the blender, and involves add-blending an aqueous crosslinking agent liquid while being stirred in a high speed (JP-A-235378/1997 (corresponding to U.S. Pat. No. 6,071,976) and JP-A-349625/1999); and a method involves spraying a particulate liquid drop of a surface-crosslinking agent to bring a water-absorbent resin powder in a row state (JP-A-246403/1992).

As to methods for surface-crosslinking water-absorbent resins using these crosslinking agents, the following methods are known: a method which involves directly adding a crosslinking agent to a water-absorbent resin powder, or a composition obtained by dissolving a crosslinking agent in a small quantity of water or a hydrophilic organic solvent, and heat-treating if necessary (JP-A-180233/1983 (corresponding to U.S. Pat. No. 4,666,983), JP-A-189103/1984, and JP-A-16903/1986 (corresponding to U.S. Pat. No. 4,734,478)); a method which involves dispersing a water-absorbent resin in a mixed solvent of water and a hydrophilic organic solvent, and adding a crosslinking agent thereto to react with the water-absorbent resin (JP-B48521/1986); and a method which involves allowing a resin to react with a crosslinking agent in an inert solvent in the presence of water (JP-B-18690/1985 (corresponding to U.S. Pat. No. 45,418,771)).

Then, when a water-absorbent resin is surface-crosslinked, the moderate permeation of a crosslinking agent to the neighborhood of a water-absorbent resin powder is an important factor, and it is necessary that its process is favorable in view of industry.

In addition, the state of the water-absorbent resin is a powder in many cases. When the water-absorbent resin includes many particulate powders such that pass through a sieve having a mesh opening size of 150 μm, it may exercise a bad influence on the working environment due to causing dust, it may cause the blendability to decrease when blending with other substances, and it may cause formation of bridge in a hopper.

Until now, known examples of production processes for water-absorbent resins having a small amount of particulate powders include a method which involves adjusting the particle diameter by adjusting the extent of the polymerization or pulverization, or a method which involves classify-removing the particulate powders as caused. However, plenty of particulate powders (several to several tens percents) are caused in the production steps even if the above method is carried out. Therefore, the yield is greatly decreased when the particulate powders are classify-removed, and further abandoned. At the same time, there are disadvantages in view of abandoning cost.

Then, various methods for modifying a water-absorbent resin for the purpose of solving the above problems are proposed by granulating or recovering the particulate powders to granules by use of binders such as an aqueous liquid, wherein the particulate powders are inevitably caused in the steps of producing the water-absorbent resin (JP-A-101536/1986 (corresponding to U.S. Pat. No. 4,734,478) and JP-A-817200/1991 (corresponding to U.S. Pat. No. 5,369,148)). Preferred binders for the water-absorbent resin generally include water or an aqueous liquid in view of efficiency, safety, and production costs.

The steps of producing such a water-absorbent resin includes an modifying step by adding and blending a liquid material, such as adding a surface-crosslinking agent to the water-absorbent resin after polymerization and drying, or blending a binder to a water-absorbent resin including powders in order to reduce dust as caused. In addition, when carrying out an antimicrobial processing, an removal of odor, and besides, an modification of giving additional functions to a water-absorbent resin, which tend to increase in recent years, the water-absorbent resin is frequently blended with antimicrobial agents, deodorants, and besides, other additives, as a liquid material.

Furthermore, when the water-absorbent resin is surface-crosslinked or modified, a liquid material is added (preferably spray-added), and then the resultant mixture is heat-treated. However, even if the water-absorbent resin is heated at the same temperature (water-absorbent resin temperature or heat medium temperature), depending upon the kind of liquid materials, the improvement of the properties might be insufficient, and the properties might not be stabilized in a continuous production process.

When producing the water-absorbent resin, the step of blending the liquid material to the water-absorbent resin is essential so as to modify its various properties with good balance, and further, to give additional functions. However, the water-absorbent resin has a property of absorbing the liquid material rapidly when the water-absorbent resin comes into contact with the liquid material. Therefore, it is difficult to blend the liquid material with the water-absorbent resin uniformly.

In addition, the water-absorbent resin has a characteristic of increasing adhesion when the water-absorbent resin absorbs a liquid. Therefore, the water-absorbent resin excessively absorbing the liquid may be formed as an adhesive or piled material in a blending apparatus. When operating the blending apparatus in order to mass-produce the water-absorbent resin, the formation of such a piled material causes an overload for a driving motor of such as a driving shaft, and is a serious problem on operating the apparatus safely.

In addition, the surface-treatment, such as forming surface-crosslinking layers in a water-absorbent resin is tried so as to modify various properties of the water-absorbent resin in good balance in the above way. However, any treatment has above-mentioned problems, and there was no sufficiently satisfactory method in view of property and industry before.

SUMMARY OF THE INVENTION

A. Object of the Invention

Accordingly, in a production process for a water-absorbent resin, comprising the steps of: blending a liquid material and a water-absorbent resin; and heating the resultant mixture in order to produce a modified water-absorbent resin, an object of the present invention is to provide: a method for uniformly and efficiently treating a water-absorbent resin favorably in view of industry, and as a result, a good-balanced water-absorbent resin having various excellent properties, such absorption capacity, absorption capacity under a load, and single-layer absorption capacity under a load in contact with an aqueous liquid.

B. Disclosure of the Invention

The present inventors diligently studied to solve the problems. As a result, they found that the problems could be solved by employing a mode of spray-blending with a specific blending apparatus and/or a mode of specific surface-treatment in a surface-treating step.

That is to say, a production process for a water-absorbent resin, according to the present invention, comprises the steps of: blending a liquid material and a water-absorbent resin; and heating the resultant mixture in order to produce a modified water-absorbent resin, and is characterized by further comprising the step of spray-blending a water-absorbent resin (A) and a liquid material (B) with a blending apparatus equipped with a spray nozzle (C), and being characterized in that the liquid material (B) is sprayed from the spray nozzle (C) and its spray pattern is a circular and hollow cone shape.

In addition, another production process for a water-absorbent resin, according to the present invention, comprises the steps of: blending a liquid material and a water-absorbent resin; and heating the resultant mixture in order to produce a modified water-absorbent resin, and is characterized by further comprising the step of spray-blending a water-absorbent resin (A) and a liquid material (B) with a blending apparatus equipped with a spray nozzle (C), and being characterized in that the liquid material (B) is sprayed from the spray nozzle (C) and its spray pattern is a double-convex-lens and elliptic cone shape.

In addition, yet another production process for a water-absorbent resin, according to the present invention, comprises the steps of: blending a liquid material (B) and a water-absorbent resin (A); and heating the resultant mixture in order to produce a modified water-absorbent resin, and is characterized by further comprising the step of heat-treating a water-absorbent resin under an atmosphere having a dew point of not higher than 60° C. and a temperature of not lower than 90° C., wherein the water-absorbent resin before modifying is obtained after a drying step following a pulverization step.

In addition, yet another production process for a water-absorbent resin, according to the present invention, comprises the steps of: blending a liquid material and a water-absorbent resin; and heating the resultant mixture in order to produce a modified water-absorbent resin, and further comprises the steps of: spray-blending a water-absorbent resin (A) and a liquid material (B) with a blending apparatus equipped with a spray nozzle (C); and heat-treating, with the production process being characterized in that the liquid material (B) is sprayed from the spray nozzle (C) and its spray pattern is a circular and hollow cone shape in the spray-blending step, and in that the heat-treating step is carried out under an atmosphere having a dew point of not higher than 60° C. and a temperature of not lower than 90° C.

In addition, yet another production process for a water-absorbent resin, according to the present invention, comprises the steps of: blending a liquid material and a water-absorbent resin; and heating the resultant mixture in order to produce a modified water-absorbent resin, and further comprises the steps of: spray-blending a water-absorbent resin (A) and a liquid material (B) with a blending apparatus equipped with a spray nozzle (C); and heat-treating, with the production process being characterized in that the liquid material (B) is sprayed from the spray nozzle (C) and its spray pattern is a double-convex-lens and elliptic cone shape in the spray-blending step, and in that the heat-treating step is carried out under an atmosphere having a dew point of not higher than 60° C. and a temperature of not lower than 90° C.

In addition, a water-absorbent resin, according to the present invention, is surface-crosslinked with a surface-crosslinking agent including at least a polyhydric alcohol, has a particle size distribution such that the ratio of particles having particle diameters of smaller than 150 μm is not more than 5 weight %, and exhibits an absorption capacity without a load of not less than 30 g/g, with the water-absorbent resin being characterized in that: the single-layer absorption capacity (10 min.) of particles having particle diameters of 600 to 300 μm is not less than 30 g/g under a load; the single-layer absorption capacity (60 min.) of particles having particle diameters of 600 to 300 μm is not less than 30 g/g under a load; the single-layer absorption capacity (10 min.) of particles having particle diameters of 300 to 150 μm is not less than 30 g/g under a load; and the single-layer absorption capacity (60 min.) of particles having particle diameters of 300 to 150 μm is not less than 30 g/g under a load.

In addition, a water-absorbent resin, according to the present invention, is surface-crosslinked with a surface-crosslinking agent including at least a polyhydric alcohol, has a particle size distribution such that the ratio of particles having particle diameters of smaller than 150 μm is not more than 5 weight %, and exhibits an absorption capacity without a load of not less than 30 g/g, with the water-absorbent resin being characterized in that the index of uniform surface-treatment is not less than 0.70.

In addition, a sanitary material, according to the present invention, comprises the water-absorbent resin according to the present invention.

These and other objects and the advantages of the present invention will be more fully apparent from the following detailed disclosure.

Figure 1:
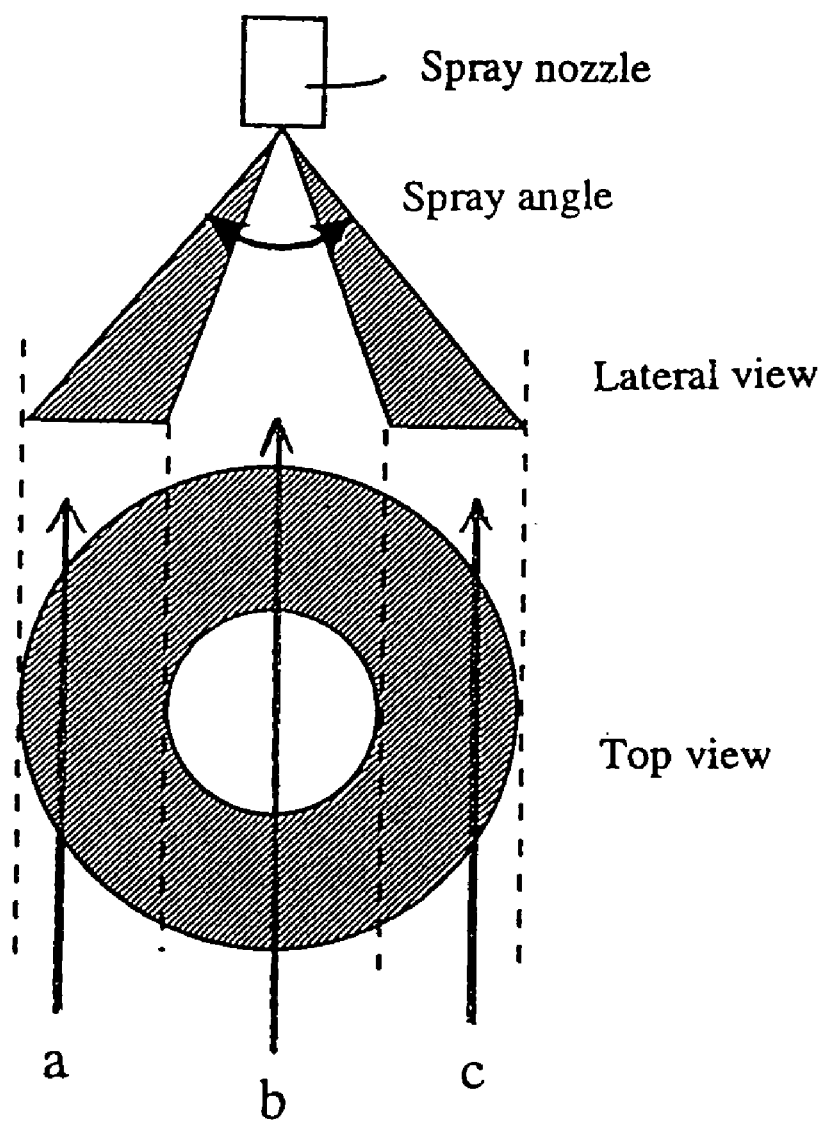
FIG. 1 is a schematic view of the spray pattern of the circular and hollow cone shape (a hollow cone spray shape), which is used for producing water-absorbent resins according to the present invention.

(Explanation of the Symbols)
1: Balance
2: Vessel
3: Air-inhaling pipe
4: Introducing tube
5: Measurement part
6: Glass filter
7: Filter paper
8: Supporting cylinder
9: Wire net
10: Weight
11: Physiological saline solution or synthetic urine

DETAILED DESCRIPTION OF THE INVENTION

Hereinafter, the present invention is explained in detail.
(Water-Absorbent Resin Before Modifying):

The water-absorbent resin added to the liquid material is not especially limited in the present invention, and can fitly be determined according to its use. However, a hydrophilic crosslinking polymer having a carboxyl group is preferably used. The hydrophilic crosslinking polymer is a conventional water-absorbent resin which is obtained by polymerizing hydrophilic monomers comprising a major proportion of either or both of acrylic acid and its salt (neutralized product), and forms a hydrogel in water due to the absorption of as large an amount of water as 50 to 1,000 times of themselves.

The acid group of the hydrophilic crosslinking polymer is more preferably neutralized with alkali metal salts, ammonium salts, or amine salts, for example, preferably in a ratio of 30 to 100 mol %, more preferably 50 to 90 mol %, particularly preferably 60 to 80 mol %. The polymerization reaction may be started after the beforehand neutralizing this acid group in a step of preparing a hydrophilic unsaturated monomer before obtaining the hydrophilic crosslinking polymer, or the acid group of the hydrophilic crosslinking polymer as obtained during or after the polymerization reaction may be neutralized, or these may be combined each other.

The hydrophilic unsaturated monomer may include unsaturated monomers other than acrylic acid or its salt (hereinafter, referred as other monomers) when the occasion demands. Example of the other monomer include: anionic unsaturated monomers, such as methacrylic acid, maleic acid, vinylsulfonic acid, styrenesulfonic acid, 2-(meth)acrylamido-2-methylpropanesulfonic acid, 2-(meth)acryloylethanesulfonic acid, and 2-(meth)acryloylpropanesulfonic acid, and their salts; nonionic unsaturated monomers containing hydrophilic groups, such as acrylamide, methacrylamide, N-ethyl(meth)acrylamide, N-n-propyl(meth)acrylamide, N-isopropyl(meth)acrylamide, N,N-dimethyl(meth)acrylamide, 2-hydroxyethyl (meth)acrylate, 2-hydroxypropyl (meth)acrylate, methoxypolyethylene glycol (meth)acrylate, polyethylene glycol mono(meth)acrylate, vinylpyridine, N-vinylpyrrolidone, N-acryloylpiperidine, and N-acryloylpyrrolidine; and cationic unsaturated monomers such as N,N-dimethylaminoethyl (meth)acrylate, N,N-diethylaminoethyl (meth)acrylate, N,N-dimethylaminopropyl (meth)acrylate, N,N-dimethylaminopropyl (meth)acrylamide, and their quaternary salts. However, the other monomers are not especially limited thereto. When these other monomers are jointly used, the amount as used is preferably not more than 30 mol %, more preferably not more than 10 mol %, of the entirety of the hydrophilic unsaturated monomer.

The water-absorbent resin as obtained by polymerizing the hydrophilic unsaturated monomer preferably has carboxyl groups. The amount of the carboxyl group in the water-absorbent resin is not especially limited, but is preferably not less than 0.01 equivalent per 100 g of the water-absorbent resin.

When obtaining the water-absorbent resin, a crosslinked structure is desirably introduced into the polymer by using an internal-crosslinking agent. The above-mentioned internal-crosslinking agent may be a compound having a plurality of polymerizable unsaturated groups and/or reactive groups to the carboxyl group per molecule, and is not especially limited. That is to say, the internal-crosslinking agent may be a compound having a plurality of substituent groups copolymerizable with the hydrophilic unsaturated monomer and/or reactive to the carboxyl group of the carboxyl hydrophilic unsaturated monomer per molecule. Incidentally, the hydrophilic unsaturated monomer may comprise a self-crosslinking compound which forms the crosslinked structure even if the internal-crosslinking agent is not used.

Examples of the above-mentioned internal-crosslinking agent include N,N'-methylenebis(meth)acrylamide, poly) ethylene glycol di(meth)acrylate, (poly)propylene glycol di(meth)acrylate, trimethylolpropane tri(meth)acrylate, trimethylolpropane di(meth)acrylate, glycerol tri(meth)acrylate, glycerol acrylate methacrylate, ethoxylated trimethylolpropane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth)allyloxyalkanes, (poly)ethylene glycol diglycidyl ether, glycerol diglycidyl ether, ethylene glycol, polyethylene glycol, propylene glycol, glycerin, pentaerythritol, ethylenediamine, polyethylenimine, and glycidyl (meth)acrylate. However, the internal-crosslinking agent is not especially limited. These internal-crosslinking agents are used either alone respectively or in combinations with each other. Among the exemplified internal-crosslinking agents, those having a plurality of polymerizable unsaturated groups per molecule are preferably used because they can give a water-absorbent resin of which the properties are more modified.

The amount of the internal-crosslinking agent as used is preferably in the range of 0.005 to 3 mol %, more preferably, 0.01 to 1.5 mol %, of the above-mentioned monomer. In the case where the amount of the above-mentioned internal-crosslinking agent as used is smaller than 0.005 mol % or larger than 3 mol %, water-absorbent resins having desired properties might not be obtained.

Incidentally, when the hydrophilic unsaturated monomer is polymerized in order to obtain the water-absorbent resin, the following materials may be added to the reaction system: hydrophilic polymers such as starch-cellulose, derivatives of starch-cellulose, polyvinyl alcohol, polyacrylic acid (or its salts), and crosslinked polyacrylic acid (or its salts); chain transfer agents such as hypophosphorous acid (or its salts); chelating agents; and water-soluble or water-dispersible surfactants.

The method for polymerizing the hydrophilic unsaturated monomer is not especially limited. For example, conventional methods such as aqueous solution polymerization, reversed-phase suspension polymerization, bulk polymerization and precipitation polymerization, are available. Among these polymerizations, methods in which an aqueous solution of the hydrophilic unsaturated monomer is prepared and then polymerized, namely, the aqueous solution polymerization or reversed-phase suspension polymerization in consideration of the easiness of the polymerization reaction control and the performance of the resultant water-absorbent resin.

In the above polymerization method, the concentration of the aqueous monomer component solution, namely, the ratio of the monomer component in the aqueous solution is not especially limited, but is preferably not less than 10 weight %, more preferably in the range of 10 to 65 weight %, still more preferably 10 to 50 weight %, most preferably 15 to 40 weight %. In addition, the reaction conditions such as reaction temperature and reaction time may fitly be set for the monomer component as used, and are not especially limited.

When polymerizing the hydrophilic unsaturated monomers, the following can be used: radical polymerization initiators, such as potassium persulfate, ammonium persulfate, sodium persulfate, t-butyl hydroperoxide, hydrogen peroxide, and 2,2'-azobis(2-amidinopropane) dihydrochloride; and active energy lights, such as ultraviolet, and electron beam. In addition, when using the oxidative radical polymerization initiators, they may be combined with reducing agents, such as sodium sulfite, sodium hydrogen sulfite, iron (II) sulfate, and L-ascorbic acid, thereby carrying out redox polymerization. The amount of these polymerization initiators as used is preferably in the range of 0.001 to 2 mol %, more preferably 0.01 to 0.5 mol %.

The solid content of the hydrogel polymer as obtained by the above-mentioned polymerization is adjusted by drying. The drying of the hydrogel polymer can be carried out by using conventional dryers and heating furnaces, such as thin blending dryers, rotary dryers, disk dryers, fluidized-bed dryers, air blow type dryers, and infrared dryers. Then, the drying temperature is preferably in the range of 40 to 250° C., more preferably 90 to 200° C., still more preferably 120 to 180° C. The solid content of the dry product as obtained in the above way is usually in the range of 70 to 100 weight % (water content: 30 to 0 weight %), preferably 80 to 98 weight % (water content: 20 to 2 weight %), most preferably 90 to 98 weight % (water content: 10 to 2 weight %). Incidentally, the solid content is usually calculated from the amount as decreased by drying at 180° C. for 3 hours.

The dry product as obtained in the above drying can be used as a water-absorbent resin as it is. However, the dry product can be used as a particulate water-absorbent resin having a predetermined size by pulverization and classification. Then, the particle size is not larger than 2 mm, preferably in the range of 10 µm to 1 mm. The weight-average particle diameter may be different depending upon its use, but is in the range of 100 to 1,000 µm, preferably 150 to 800 µm, still more preferably 300 to 600 µm. In addition, the ratio of the particles passing through a sieve having a mesh opening size of 150 µm is preferably not more than 15 weight %, more preferably not more than 10 weight %, still not more than 5 weight %.

The water-absorbent resin as obtained may be in various shapes, such as spherical shapes, flake shapes, irregular pulverized shapes, fiber shapes, granular shapes, stick shape, conventional round shapes, and flat shapes.

In addition, the content of an uncrosslinked polymer in the water-absorbent resin, namely, the extractable content is preferably not more than 30 weight %, more preferably not more than 20 weight %, still more preferably not more than 10 weight %.

In addition, the present invention process is favorably applied to water-absorbent resins having high absorption capacity, which were difficult to uniformly blend with the liquid material in the past, and is applied to water-absorbent resins having a water absorption capacity without load of preferably not less than 30 g/g, more preferably 35 to 100 g/g, still more preferably 40 to 90 g/g, particularly preferably 45 to 85 g/g.

In the present invention, the water-absorbent resin as obtained in the above way is spray-blended with the liquid material with a specific blending apparatus, and/or specifically heat-treated. Hereinafter, these are explained one by one.

(Step of Spray-Blending Liquid Material):

In the present invention, the liquid material is added to the water-absorbent resin as obtained in the above way from the spray nozzle, and further modified. The modification by adding the liquid material in the present invention includes at least one selected from among the following surface-crosslinking, granulation, and addition of additives. Incidentally, a water-absorbent resin before adding the liquid material (B) is simply referred as the water-absorbent resin (A), and the water-absorbent resin (A) after adding the liquid material (B) is referred as a modified or surface-crosslinked water-absorbent resin.

The powder temperature of the water-absorbent resin (A) as obtained in the above way before adding the liquid material (B) is preferably adjusted to the range of 80 to 35° C., more preferably 70 to 35° C., still more preferably 50 to 35° C. Thereafter, the liquid material (B) is blended therewith. In case where the temperature of the water-absorbent resin (A) before adding the liquid material (B) is higher, the liquid material (B) is blended ununiformly. In addition, there are disadvantages in adjusting to lower than 35° C., because it takes much time to forcibly or stationary cool, and besides, the agglomeration of the powder as stationary cooled is observed, and the energy loss is increased when carrying out reheating.

When the surface neighborhood of the water-absorbent resin (A) before surface-crosslinking is further crosslinked, the liquid material (B) includes a surface-crosslinking agent, and is spray-blended with the spray nozzle (C) having the below-mentioned specific spray pattern. In addition, the resultant mixture was heat-treated, and then, the water-absorbent resin (A) is surface-crosslinked.

The surface-crosslinking agent as comprised in the liquid material (B) is not especially limited if it is a compound which has a plurality of functional groups in one molecule reactive upon a carboxyl group of the water-absorbent resin (A) and can form a covalent bond by the crosslinking reaction.

Examples of the above surface-crosslinking agent include: polyhydric alcohols, such as ethylene glycol, propylene glycol, glycerol, pentaerythritol, sorbitol, diethylene glycol, triethylene glycol, tetraethylene glycol, dipropylene glycol, tripropylene glycol, 1,3-butane diol, 1,4-butanediol, 1,5-pentanediol, 2,4-pentanediol, 1,6-hexanediol, 2,5-hexanediol, and trimethylolpropane; polyamine compounds, such as diethanolamine, triethanolamine, ethylenediamine, diethylenetriamine, and triethylenetetramine; polyglycidyl compounds, such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, and polypropylene glycol diglycidyl ether; 2,4-tolylene diisocyanate, ethylene carbonate (1,3-dioxolan-2-one), propylene carbonate (4-methyl-1,3-dioxolan-2-one), 0,4,5-dimethyl-1,3-dioxolan-2-one, (poly-, di- or mono-) 2-oxazolidinone, epichlorohydrin, epibromohydrin, diglycol silicate, and polyaziridine compounds, such as 2,2-bis(hydroxymethylbutanol)-tris[3-(1-aziridyl)propionate]. However, the surface-crosslinking agent is not limited to these compounds. In addition, these surface-crosslinking agents are used either alone respectively or in combinations with each other. Among these, at least one kind of the surface-crosslinking agents is preferably a surface-crosslinking agent selected from the group consisting of polyhydric alcohols, polyglycidyl compounds, 1,3-dioxolan-2-on, poly(2-oxazolidinone), bis(2-oxazolidinone), and mono(2-oxazolidinone), and is more preferably a surface-crosslinking agent including polyhydric alcohols.

The polyhydric alcohol is a safe surface-crosslinking agent with which the surface-crosslinking gives high properties to the water-absorbent resin, but which was difficult to uniformly blend with the water-absorbent resin because of high viscosity and/or hydrophilicity of the polyhydric alcohol. However, in the present invention, an aqueous solution including the polyhydric alcohol as the surface-crosslinking agent can preferably be used.

The amount of the surface-crosslinking agent as used, depends on the compounds as used as such, or on combinations thereof, but is preferably in the range of 0.001 to 5 parts by weight, more preferably 0.005 to 2 parts by weight, per 100 parts by weight of the solid content of the water-absorbent resin (A). In case where the amount of the surface-crosslinking agent as used is more than the above range, there are disadvantages in that: it is not only uneconomical but also the amount of the surface-crosslinking agent is excessive to form the most suitable crosslinking structure in the water-absorbent resin (A). In addition, in case where the amount of the surface-crosslinking agent as used is less than the above range, it might be difficult to obtain a surface-crosslinked water-absorbent resin having a higher absorption capacity under a load.

When the water-absorbent resin (A) is blended with the surface-crosslinking agent, water is preferably used as a solvent, and the liquid material (B) is preferably in a form of an aqueous surface-crosslinking agent solution. The amount of water as used depends upon factors such as the type, or the particle diameter of the water-absorbent resin (A), but is preferably more than 0 part by weight and not more than 20 parts by weight, more preferably in the range of 0.5 to 10 parts by weight, per 100 parts by weight of the solid content of the water-absorbent resin (A).

When the water-absorbent resin (A) is blended with the surface-crosslinking agent, a hydrophilic organic solvent may further be used, if necessary. Examples of the hydrophilic organic solvent include: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy(poly)ethylene glycol; amides such as e-caprolactam and N,N-dimethylformamide; and sulfoxides such as dimethyl sulfoxide. The amount of the hydrophilic organic solvent as used depends upon factors such as the type, or particle diameter of the water-absorbent resin (A), but is preferably less than 20 parts by weight, more preferably in the range of 0.1 to 10 parts by weight, still more preferably 0 to 5 parts by weight, particularly preferably 0 to 1 part by weight, per 100 parts by weight of the solid content of the water-absorbent resin (A). However, in the present invention, the uniform blending can be accomplished without using the hydrophilic organic solvents particularly because of excellent mixability.

In addition, the liquid temperature of the liquid material (B) is preferably lower than the powder temperature of the water-absorbent resin (A), more preferably lower than the powder temperature of the water-absorbent resin (A) by 10° C., still more preferably by 20° C., most preferably by 30° C. Incidentally, the liquid material (B) is sprayed from the spray nozzle (C). Therefore, its liquid temperature should be higher than its melting point. In addition, when the liquid temperature of the liquid material (B) is too high, there are disadvantages in that: the liquid absorption speed is rapid, and the uniform blending of the liquid material (B) and the water-absorbent resin (A) is inhibited.

When the water-absorbent resin (A) is blended with the aqueous surface-crosslinking agent solution in the present invention, the aqueous surface-crosslinking agent solution, namely, the liquid material (B) spray-blended with the water-absorbent resin (A) by use of the blender equipped with the specific spray nozzle (C).

The average diameter of the liquid drop of the liquid material (B) as blended with the water-absorbent resin (A) is preferably smaller than the average diameter of the water-absorbent resin (A), and is more preferably not larger than 300 μm, still more preferably not larger than 250 μm. The average diameter of the liquid drop is usually in the range of 50 to 200 μm. In case where the average diameter is larger than 300 μm, there are disadvantages in that: it is difficult to defuse or disperse the liquid material (B) uniformly; a lump having high density is caused; and the amount of the water-absorbent resin (A) which does not come into contact with the liquid material (B), namely, the aqueous surface-crosslinking agent solution is increased in the blending apparatus.

In the present invention, the spray angle of the liquid material (B) from the spray nozzle (C) is very important, and the maximum spray angle of the liquid material (B) from the spray nozzle (C) is preferably not less that 50°.

The production process, according to the present invention, is characterized in that: the liquid material (B) is sprayed from the spray nozzle (C) and its spray pattern is a circular and hollow cone shape (a hollow cone spray shape); or the liquid material (B) is sprayed from the spray nozzle (C) and its spray pattern is a double-convex-lens and elliptic cone shape (a flat spray shape). In these processes, the maximum spray angle is preferably is not less than 50°.

Figure 2:
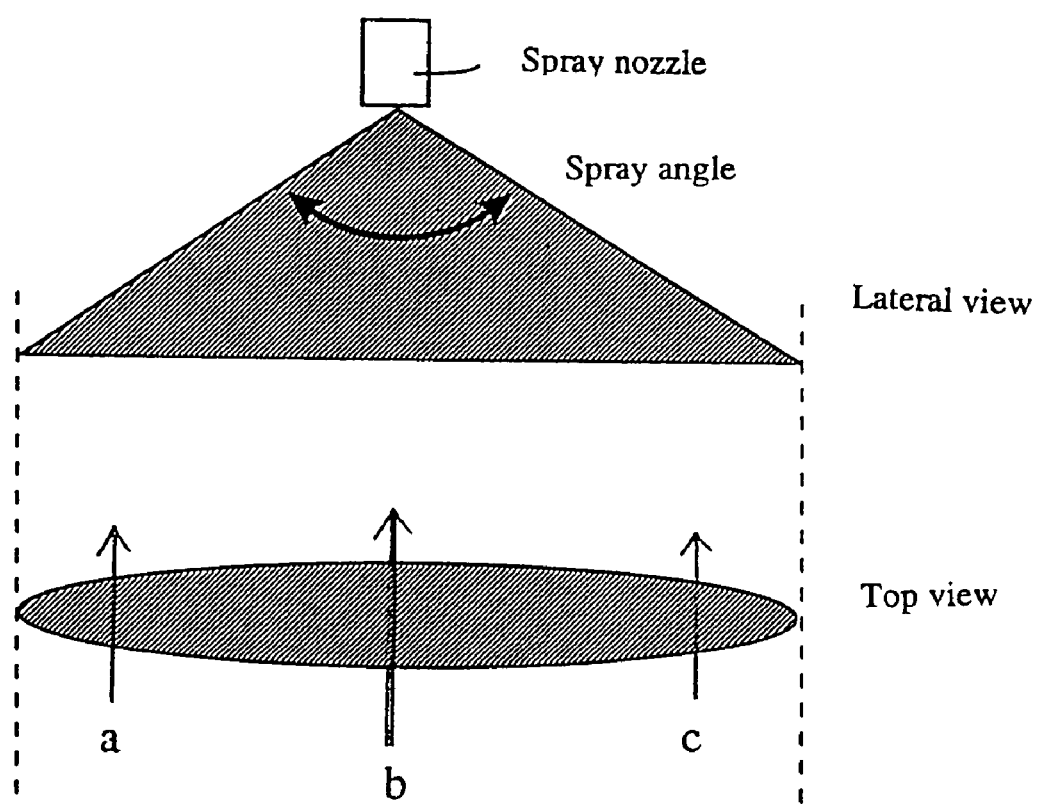
FIG. 2 is a schematic view of the spray pattern of the double-convex-lens and elliptic cone shape (a flat spray shape), which is used for producing water-absorbent resins according to the present invention.

The schematic figures of the spray angle and the spray pattern of the spray nozzle (C) are illustrated in FIG. 1 (spraying in a circular and hollow cone shape (a hollow cone spray shape)) and FIG. 2 (spraying in a double-convex-lens and elliptic cone shape (a flat spray shape)). However, the spray angle is changed depending upon the viscosity and temperature of the liquid material (B) sprayed from the spray nozzle (C). In addition, when the spray nozzle (C) is a hydraulic nozzles (liquid-pressurized nozzles sprayed only by fluid pressure), the spray angle is changed due to the amount of the liquid material (B) as sprayed and its spray pressure. When the spray nozzle (C) is a pneumatic nozzles (air- and liquid-pressurized nozzles (sprayed with compressed air)), the spray angle is changed due to the amount of the liquid material (B) as sprayed, the air pressure, and the amount of air as consumed.

As is illustrated in FIG. 1, when the liquid material (B) is sprayed from the spray nozzle (C) in a circular and hollow cone shape (a hollow cone spray shape), and for example, the water-absorbent resin (A) is transferred toward arrowed directions (a, b, and c) in FIG. 1, the amount as sprayed at end portions a and c, and the amount as sprayed in the center portion b vary little while being transferred. As a result, the uniform spraying can be realized.

As is illustrated in FIG. 2, when the liquid material (B) is sprayed from the spray nozzle (C) in a double-convex-lens and elliptic cone shape (a flat spray shape), and for example, the water-absorbent resin (A) is transferred toward arrowed directions (a, b, and c) in FIG. 2, the amount as sprayed at end portions a and c, and the amount as sprayed in the center portion b vary little while being transferred. As a result, the uniform spraying can be realized.

The spray nozzle (C) is necessary to be fitly selected according to the use condition so that the spray nozzle (C) has a predetermined spray angle. However, the spray angle of the liquid material (B) from the spray nozzle (C) is preferably selected at not less than 50°, more preferably not less than 70°, still more preferably not less than 90°. In case where the spray angle is less than 50°, the portion where the liquid material (B) is dispersed excessively and the portion where the liquid material (B) is dispersed in low density are caused in a dispersing state of the liquid material (B) as sprayed in the blending apparatus, and the partiality is caused in a blending state of the water-absorbent resin (A) and the liquid material (B). There are disadvantages in that the water-absorbent resin (A) as excessively brought into contact with the liquid material (B), namely, the aqueous surface-crosslinking agent solution produces a lump having high density (rigid agglomerated material) easily, and causes excessive surface-crosslinking. This lump having high density becomes a rigid lump difficult to pulverize after the heat treatment as described in the following. Therefore, the extra-pulverization is necessary in order to adjust to the particle size of the produced material (for example, all the particles have a particle size of less than 1 mm.). However, where the pulverization is carried out, there are disadvantages in that the surface-crosslinked layer as specially formed is destroyed by pulverization. Incidentally, the maximum spray angle is not more than 180° because of the structure of the spray.

In addition, there are disadvantages in that the water-absorbent resin (A) as excessively brought into contact with the liquid material (B) is easily adhered and piled in the blending apparatus in view of the stable operation of the apparatus. Furthermore, when the portion where the liquid material (B) is excessively dispersed comes into contact with the portion of the blending apparatus, there are disadvantages in that the liquid drop is easily produced and the formation of the piled material is caused in the apparatus.

On the other hand, there are disadvantages in that the desirable crosslinking effect is not possibly obtained in the water-absorbent resin (A) as brought into contact with the liquid material (B) in low density.

In addition, the present invention process which involves the maximum spray angle of the liquid material (B) from the spray nozzle (C) at not less than 50°, the process which involves spraying the liquid material (B) from the spray nozzle (C) with a spray pattern of a circular and hollow cone shape (a hollow cone spray shape), or the process which involves spraying the liquid material (B) from the spray nozzle (C) with a spray pattern of a double-convex-lens and elliptic cone shape (a flat spray shape) is more preferably applied to continuous production processes. Incidentally, the maximum spray angle is not more than 180° because of the structure of the spray.

Furthermore, when the liquid material (B) is sprayed from the spray nozzle (C) for the purpose of adjusting to the above predetermined spray angle, the area of the spray-dispersing state of the liquid material (B) projected onto a sectional area which is perpendicular to the axis direction of the blending apparatus and includes a spraying point of the spray nozzle (C) preferably accounts for 70 to 100% of the sectional area perpendicular to the axis direction of the blending apparatus, more preferably 80 to 100%, still more preferably 90 to 100%. In case where the area of the spray-dispersing state of the liquid material (B) projected onto a sectional area which is perpendicular to the axis direction of the blending apparatus and includes the spraying point of the spray nozzle (C) preferably accounts for less than 70% of the sectional area perpendicular to the axis direction of the blending apparatus, there are disadvantages in that the portion where the liquid material (B) is dispersed excessively and the portion where the liquid material (B) is dispersed in low density are caused in a dispersing state of the liquid material (B) as sprayed in the blending apparatus, and the partiality is caused in a blending state of the water-absorbent resin (A) and the liquid material (B).

The number of the spray nozzles (C) with which the blending apparatus is equipped may be one or more. The number is preferably two or more so that the area of the spray-dispersing state projected onto a sectional area including the spraying point of the spray nozzle (C) would enlarge.

The blending apparatus as used for blending the water-absorbent resin (A) and the liquid material (B) is desired to have strong blending power, and the water-absorbent resin is preferably stirred or fluidized by flowing gas, so that both would be uniformly and surely blended. Examples of the above blending apparatus include: cylinder type blenders, double-walls cone type blenders, V-character-shaped blenders, ribbon type blenders, screw type blenders, fluid type rotary disk blenders, air current type blenders, double-arm type kneaders, internal blenders, pulverization type blenders, rotary blenders, and screw type extruders. However, a high-speed agitation type blending apparatus comprising an agitation shaft having a plurality of paddles is preferable. Herein, the high-speed agitation type blending apparatus means a blender which obtains blending power by rotating the agitation shaft having a plurality of paddles usually with 100 to 5,000 rpm, preferably 200 to 4,000 rpm, more preferably 500 to 3,000 rpm.

In addition, the inner wall of the blending apparatus is preferably made of a low adhesive material such as Teflon in order to prevent the mixture of the water-absorbent resin (A) and the liquid material (B) from adhering and piling.

Furthermore, the inner wall temperature of the blending apparatus is preferably higher than room temperature, more preferably not lower than 40° C. The temperature is preferably maintained in the range of 50 to 100° C. In addition, the inner wall temperature of the blending apparatus is preferably higher than the temperature of water-absorbent resin (A). The temperature difference is preferably not more than 40° C., more preferably not more than 20° C. In case where the inner wall temperature of the blending apparatus is not higher than room temperature, when the liquid material (B) and water-absorbent resin (A) are blended, there is a possibility that the resultant water-absorbent resin mixture is adhered to the inner wall or piled.

The modification carried out by adding the liquid material (B), according to the present invention, can be widely applied typically to addition of the surface-crosslinking agent in the surface-crosslinking of the water-absorbent resin. However, there is no especial limitation thereto. For example, the modification can be applied to granulation of water-absorbent resins and mixing thereof with additives besides the addition of the surface-crosslinking agent. The water-absorbent resin (A) which would be granulated or added to the liquid material (B) as additives may be surface-crosslinked, a water-absorbent resin before surface-crosslinking (usually water-absorbent resin obtained only by polymerization and drying), the water-absorbent resin surface-crosslinked by the present invention production process, or other surface-crosslinked water-absorbent resin (for example, surface-crosslinking in dispersive systems, such as reversed-phase suspension). However, particularly, the granulation is carried out or other additive is added preferably by adding the liquid material (B) to the water-absorbent resin surface-crosslinked by the present invention production process.

Hereinafter, in the production process for a water-absorbent resin, which comprises the step of spray-blending the water-absorbent resin (A) and the liquid material (B) with the blending apparatus equipped with the spray nozzle (C), with the production process being characterized in that the liquid material (B) is sprayed from the spray nozzle (C) and its spray pattern is a circular and hollow cone shape (a hollow cone spray shape) or a double-convex-lens and elliptic cone shape (a flat spray shape), it is further explained that the modification is carried out by granulating the water-absorbent resin or blending additives.

When the occasion demands, the water-absorbent resin (A) is granulated to a granule by use of the liquid material (B) as a binder, and the ratio of particles passed through a mesh opening size of 150 µm can be decreased.

The powder temperature of the above water-absorbent resin (A) is preferably adjusted to the range of 80 to 35° C., more preferably 70 to 35° C., still more preferably 50 to 35° C. Thereafter, the liquid material (B) is blended therewith. In case where the temperature of the water-absorbent resin (A) before adding the liquid material (B) is higher, the liquid material (B) is blended ununiformly. In addition, there are disadvantages in adjusting to lower than 35° C., because it takes much time to forcibly or stationary cool, and besides, the agglomeration of the powder as stationary cooled is observed, and the energy loss is increased when carrying out reheating.

Water only or an aqueous liquid is preferably used as the binder in view of efficiency, safety, and cost.

When the aqueous liquid is used as the binder, example thereof include materials obtained by dissolving the above exemplified hydrophilic organic solvents and/or water-soluble polymers, such as poly(acrylic acid (salt)), carboxymethyl cellulose, hydroxyethyl cellulose, and polyethylene glycol.

In addition, for the purpose of modifying by giving various additional functions, additives such as disinfection, deodorization to the water-absorbing agent, antimicrobial agents, deodorants, perfumes, food additives, oxidizing agents, reducing agents, chelating agents, antioxidants, radical inhibitors, and colorants may be added as the liquid material (B) (if necessary, by dissolving or dispersing them in solvents). The above antimicrobial agents, deodorants, perfumes, food additives, oxidizing agents, reducing agents, chelating agents, antioxidants, radical inhibitors, and colorants may be added with the aqueous surface-crosslinking agent solution or the binder at the same time of the surface treatment or the granulation, or may be added separately.

The above antimicrobial agents are conventional disinfectant ones, and are not especially limited. Examples thereof include antimicrobial agents shown in JP-A-267500/1999.

In addition, the above deodorants are conventional ones which deodorize unpleasant components of human urine, such as mercaptan, hydrogen sulfide, and ammonia, and are not especially limited. Examples thereof include plant extracts from camellias of which deodorizing components are, for examples, flavanols or flavonols.

The amount of the binder and/or the additive for the purpose of giving additional functions to the water-absorbent resin as added can fitly be changed, depending on the purpose of addition and the kind of the additive. However, the binder and/or the additive is usually added in the range of preferably 0.001 to 10 parts by weight, more preferably 0.01 to 5 parts by weight, still more preferably 0.05 to 1 part by weight, per 100 parts by weight of the water-absorbent resin (A).

The amount of the solvent (preferably water) of the binder and/or the additive as used for the purpose of giving additional functions to the water-absorbent resin is preferably in the range of 1 to 30 parts by weight, more preferably 1 to 10 parts by weight, per 100 parts by weight of the water-absorbent resin (A). In case where the amount as used is less than 1 part by weight, the granulation is insufficient and the additive is blended ununiformly. In reverse, in case where the amount is more than 30 parts by weight, a lump having high density is easily caused and becomes a rigid lump difficult to pulverize. Therefore, the pulverization is necessary in order to adjust to the particle size of the produced material (for example, all the particles have a particle size of less than 1 mm.). However, when the surface-crosslinking is carried out in the above process, there are disadvantages in that the surface-crosslinked layer as specially formed might be destroyed by pulverization.

In addition, the liquid temperature of the liquid material (B) is preferably lower than the powder temperature of the water-absorbent resin (A), more preferably lower than the powder temperature of the water-absorbent resin (A) by 10° C., still more preferably by 20° C., most preferably by 30° C. Incidentally, the liquid material (B) is sprayed from the spray nozzle (C). Therefore, its liquid temperature should be higher than its melting point. In addition, when the liquid temperature of the liquid material (B) is too high, there are disadvantages in that: the liquid absorption speed is rapid, and the uniform blending of the liquid material (B) and the water-absorbent resin (A) is inhibited.

The average diameter of the liquid drop of the liquid material (B) as the binder and/or the additive blended with the water-absorbent resin (A), for the purpose of giving the additional functions to the water-absorbent resin, is preferably smaller than the average diameter of the water-absorbent resin (A), and is more preferably not larger than 300 µm, still more preferably not larger than 250 µm. The average diameter of the liquid drop is usually in the range of 50 to 200 µm. In case where the average diameter is larger than 300 µm, there are disadvantages in that: it is difficult to defuse or disperse the liquid material (B) uniformly; a lump having high density is caused; and the amount of the water-absorbent resin (A) which does not come into contact with the liquid material (B) is increased in the blending apparatus.

In addition, the spray nozzle (C) is necessary to be fitly selected according to the use condition so that the spray nozzle (C) has a predetermined spray angle. However, the spray angle of the liquid material (B) from the spray nozzle (C) is preferably selected at not less than 50°, more preferably not less than 70°, still more preferably not less than 90°. In case where the spray angle is less than 50°, the portion where the liquid material (B) is dispersed excessively and the portion where the liquid material (B) is dispersed in low density are caused in a dispersing state of the liquid material (B) as sprayed in the blending apparatus, and the partiality is caused in a blending state of the water-absorbent resin (A) and the liquid material (B). The water-absorbent resin (A) as excessively brought into contact with the liquid material (B) produces a lump having high density easily, and it becomes a rigid lump difficult to pulverize. Therefore, the pulverization is necessary in order to adjust to the particle size of the produced material (for example, all the particles have a particle size of less than 1 mm.). However, when the surface-crosslinking is carried out in the above process, there are disadvantages in that the surface-crosslinked layer as specially formed might be destroyed by pulverization. Incidentally, the maximum spray angle is not more than 180° because of the structure of the spray.

In addition, there are disadvantages in that the water-absorbent resin (A) as excessively brought into contact with the liquid material (B) is easily adhered and piled in the blending apparatus in view of the stable operation of the apparatus. Furthermore, when the portion where the liquid material (B) is excessively dispersed comes into contact with the portion of the blending apparatus, there are disadvantages in that the liquid drop is easily produced and the formation of the piled material is caused in the apparatus.

On the other hand, there are disadvantages in that the desirable granulating effect or the additional function is not possibly obtained in the water-absorbent resin (A) as brought into contact with the liquid material (B) in low density.

Furthermore, when the liquid material (B) is sprayed from the spray nozzle (C) for the purpose of adjusting to the above predetermined spray angle, the area of the spray-dispersing state of the liquid material (B) projected onto a sectional area which is perpendicular to the axis direction of the blending apparatus and includes a spraying point of the spray nozzle (C) preferably accounts for 70 to 100% of the sectional area perpendicular to the axis direction of the blending apparatus, more preferably 80 to 100%, still more preferably 90 to 100%. In case where the area of the spray-dispersing state of the liquid material (B) projected onto a sectional area which is perpendicular to the axis direction of the blending apparatus and includes the spraying point of the spray nozzle (C) preferably accounts for less than 70% of the sectional area perpendicular to the axis direction of the blending apparatus, there are disadvantages in that the portion where the liquid material (B) is dispersed excessively and the portion where the liquid material (B) is dispersed in low density are caused in a dispersing state of the liquid material (B) as sprayed in the blending apparatus, and the partiality is caused in a blending state of the water-absorbent resin (A) and the liquid material (B).

The number of the spray nozzles (C) with which the blending apparatus is equipped may be one or more. The number is preferably two or more so that the area of the spray-dispersing state projected onto a sectional area including the spraying point of the spray nozzle (C) would enlarge.

The blending apparatus as used for blending the water-absorbent resin (A) and the liquid material (B) can be used in the same way as of the above exemplified blending apparatuses used for blending the water-absorbent resin (A) with the aqueous surface-crosslinking agent solution as the aqueous liquid (B).

The resultant mixture in the above process can be dried or heat-treated if necessary.

The resultant surface-crosslinked or modified water-absorbent resin in the above way is preferably used because it displays excellent water-retaining force and higher absorption capacity especially under a load when it is used as a sanitary material.

(Step of Heat-treating):

In the present invention, the modification of the water-absorbent resin (A), preferably the crosslinking of its surface neighborhood is carried out by blending the above-mentioned water-absorbent resin (A) with the liquid material (B) (preferably, and the aqueous surface-crosslinking agent solution), and thereafter heat-treating the resultant mixture.

Incidentally, the modification of the water-absorbent resin means the granulation of water-absorbent resins or the addition of additives, and further, examples of its modes include the surface-crosslinking by the addition of the surface-crosslinking agent. The above mentioned heat-treatment depends upon the surface-crosslinking agent as used, but is preferably carried out at a water-absorbent resin temperature (material temperature) or heat medium temperature of 60 to 250° C., more preferably 80 to 250° C., still more preferably 100 to 230° C., particularly preferably 150 to 200° C. In case where the treating temperature is lower than 60° C., the uniform crosslinked structure is not formed. Accordingly, there are disadvantages in that the crosslinked water-absorbent resin having high absorption capacity under a load cannot be obtained. In addition, the productivity is caused to lower because it takes much time to carry out the heat treatment. In case where the treating temperature is higher than 250° C., the water-absorbent resin (A) is caused to deteriorate. Accordingly, there are disadvantages in that the propertied of the surface-crosslinked water-absorbent resin are lowered. Incidentally, the above-mentioned treating temperature is preferably the water-absorbent resin temperature (material temperature) in order to control the surface-crosslinking reaction exactly.

In addition, even if the surface-crosslinking agent is not used, the heat treatment is preferably carried out at the above-mentioned temperature in order to uniformly diffuse the liquid material (B) and to improve the granulation strength of the water-absorbent resin. In addition, the heat treatment may be carried out by spraying with a blender having a function of heating, or the heating and spraying may be carried out at the same time.

In the present invention, the liquid material (B) is sprayed and the above-mentioned heat treatment is carried out. Furthermore, the atmosphere of the upper space inside of the heat-treating apparatus is also preferably adjusted to a specific range when the heat treatment is carried out.

In a heat-treating method which involves adding a liquid material to a water-absorbent resin, the reaction or modification was controlled by the water-absorbent resin temperature (material temperature) or heat medium temperature in the past. However, as long as the water-absorbent resin temperature (material temperature) or heat medium temperature was merely determined, the improvement of the properties might be insufficient, and the properties might not be stabilized in a continuous production process. The present inventors diligently studied to solve these problems. As a result, in order to improve or stabilize the properties caused by heat treatment, they solved these problems by controlling the upper space condition inside of the heat-treating apparatus while heat-treating to a specific atmosphere, wherein the upper space did not draw any attention in the past.

The present invention is accomplished by heat-treating the water-absorbent resin powder as obtained in the above way under an atmosphere inside of the upper space of the heat-treating apparatus having a dew point of not higher than 60° C. and a temperature of not lower than 90° C., preferably crosslinking the water-absorbent resin powder surface in the presence of a hydrophilic solution including the aforementioned crosslinking agent or its aqueous solution to preferably carry out a crosilnking reaction. Incidentally, the atmosphere in the present invention means the temperature and dew point of the upper space inside of the heat-treating apparatus, wherein the upper space inside includes the water-absorbent resin powder, and the temperature of the heat-treating apparatus may be equal to or different from the atmosphere.

In case where the water-absorbent resin powder having a water content of not less than 10 weight % is used, there are disadvantages in that: not only the aimed properties are not obtained but also much energy is required to obtain the atmosphere having a dew point of not higher than 60° C. and a temperature of not lower than 90° C.

Figure 4:
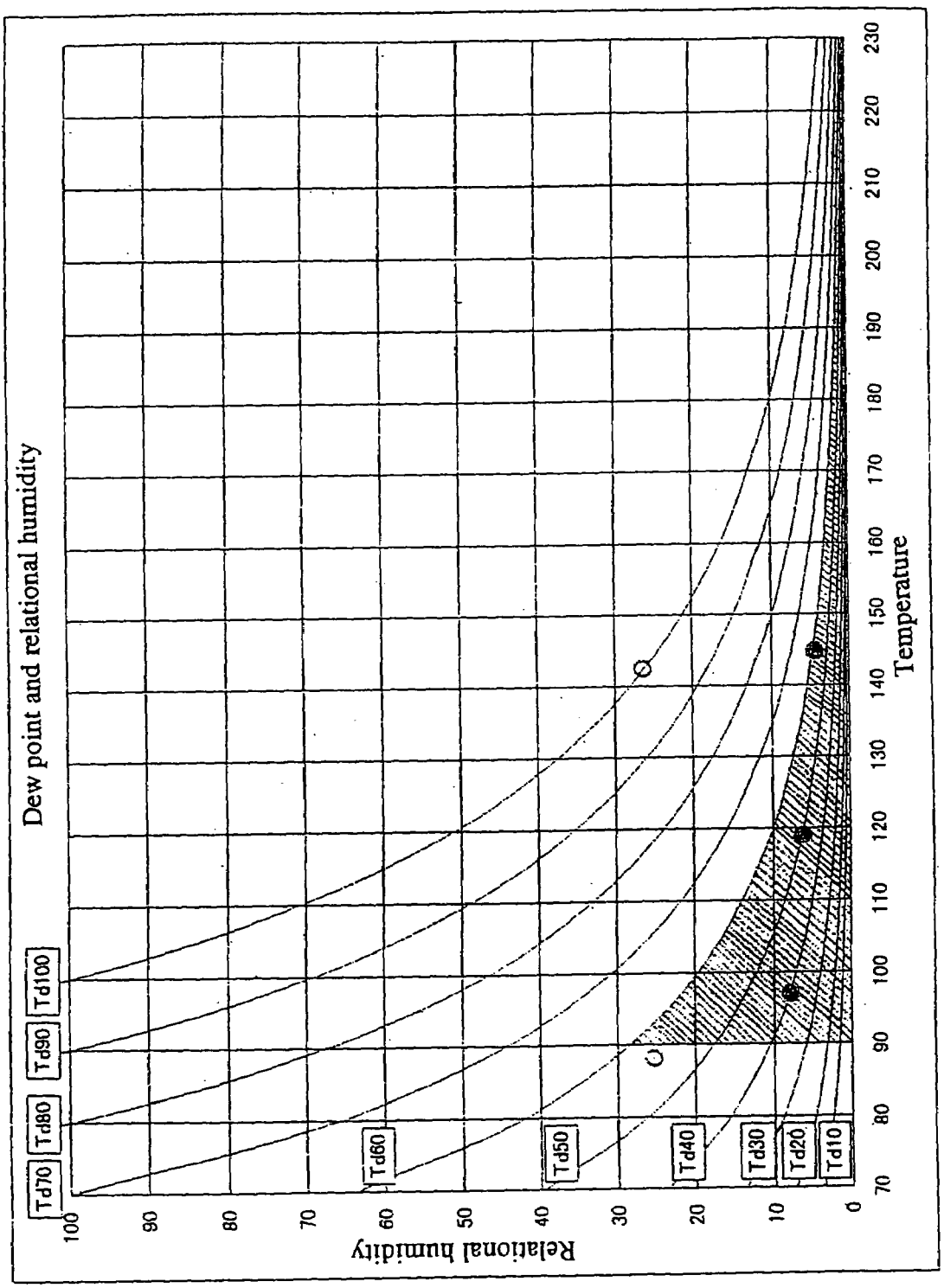
FIG. 4 is a figure showing the relationship between relational humidity and temperature (° C.) as to dew curves of vapor. In addition, the scope limited in the present invention claim is described in the hatching range. Td, black plots, and white plots mean a dew temperature, examples of the present invention, and comparative examples, respectively.

In case where the dew point is not higher than 60° C. and the temperature is not higher than 90° C., even if the water-absorbent resin temperature (material temperature) or heat medium temperature is sufficient, the crosslinking reaction between the carboxyl group on the surface of the water-absorbent resin powder and the crosslinking agent is not carried out sufficiently, and the amount of the unreacted crosslinking agent might be increased. In addition, in case where the dew point is not lower than 60° C. even if the temperature is not lower than 90° C., even if the water-absorbent resin temperature (material temperature) or heat medium temperature is sufficient, the crosslinking agent permeates into the internal portion of the water-absorbent resin powder particles, and it might be difficult to carry out the crosslinking reaction between the carboxyl group on the surface of the water-absorbent resin powder and the crosslinking agent, because the water content is slowly evaporated from the water-absorbent resin powder. Therefore, as is shown in FIG. 4, the dew point and the temperature are adjusted to not higher than 60° C. and not lower than 90° C. respectively in order to maintain the permeation of the crosslinking agent into the surface neighborhood of the water-absorbent resin powder particles in an optimum state, and to make the surface of the water-absorbent resin powder a necessary and adequate crosslinking state. It is found that the influence of the temperature and the dew point in the atmosphere especially has a great influence on the heat treatment in the surface-crosslinking, especially the heat treatment with the above-mentioned specific crosslinking agent, and further the heat treatment with the polyhydric alcohol.

As to the heat-treating apparatus to treat the water-absorbent resin powder in the above condition, conventional dryers or furnaces equipped with a gas supplying or exhausting apparatus to make the predetermined atmosphere can be used. The usable gas is vapor, air, and nitrogen, and is preferably air. The amount as supplied is fitly determined. The gas for adjusting the temperature or dew point may fitly be under reduced or compressed pressure, or may fitly be heated or cooled. Air having a nearly room temperature (for example, 0 to 50° C.) may be supplied at a substantially ordinary pressure ($1.013 \times 10^5$ Pa(1 atm)±10%, preferably ±5%, more preferably ±1%). For example, conductive-heat-transfer-type, radiative-heat-transfer-type, hot-wind-heat-transfer-type, or dielectric-heating-type dryers or furnaces equipped with a gas supplying or exhausting apparatus are favorable. Examples thereof include belt-type, channel-blending-type, rotary-type, disk-type, kneading-type, fluidized-bed-type, air-blow-type, infrared-type, or electron-beam-type dryers or furnaces equipped with an apparatus for supplying a mixed gas of air and/or an inert gas. The temperature of these heat-treating apparatuses may be equal to or different from that of the atmosphere of the upper space inside of the heat-treating apparatus, but is usually adjusted to the range of 110 to 250° C., preferably 150 to 210° C. In addition, the heat-treating apparatus is heated and its temperature is adjusted higher than the temperature of the atmosphere of the upper space inside of the heat-treating apparatus by 0 to 120° C., preferably 30 to 100° C.

Among these heat treatments, preferably by the conductive-heat-transfer or hot-wind-heat-transfer, more preferably by the conductive-heat-transfer, the water-absorbent resin is heated while being stirred or fluidized, and the atmosphere of the upper space of the treating apparatus may also be controlled, wherein the atmosphere did not draw any attention in the past. When the water-absorbent resin is heated by the conductive-heat-transfer, the water-absorbent resin is heated through the heat-transfer-surface (for example, sidewall or stirring blade of paddle-type dryer) heated by heat medium, and the upper space of the water-absorbent resin not in contact with the heat-transfer-surface may be controlled to a specific temperature and a specific dew point. Incidentally, in the present invention which involves heat-treating at the above specific dew point, the liquid material is preferably added by spray, more preferably added with the above spray pattern, and further, the resultant mixture is heat-treated. The amount as treated is not influenced by the scale of the apparatus (scale factor) even if continuously carrying out the heat treatment of 10 kg/hr, further 100 kg/hr, further more 1,000 kg/hr, still further more 2,000 kg/hr, particularly further more 3,000 kg/hr, and the liquid material is fitly used.

Incidentally, the present invention may have a mode including either or both of the step of spray-blending the liquid material and the step of heat-treating. The effect of the present invention can be displayed if the mode includes at least one selected from the group consisting of the step of spray-blending the liquid material and the step of heat-treating.

(Water-absorbent Resin According to the Present Invention):

The water-absorbent resin, according to the present invention, is preferably obtained by the production process according to the present invention, but is not limited thereto.

The water-absorbent resin, according to the present invention, is surface-crosslinked with a surface-crosslinking agent including at least a polyhydric alcohol, has a particle size distribution such that the ratio of particles having particle diameters of smaller than 150 μm is not more than 5 weight %, and exhibits an absorption capacity without a load of not less than 30 g/g, with the water-absorbent resin being characterized in that: the single-layer absorption capacity (10 min.) of particles having particle diameters of 600 to 300 μm is not less than 30 g/g under a load; the single-layer absorption capacity (60 min.) of particles having particle diameters of 600 to 300 μm is not less than 30 g/g under a load; the single-layer absorption capacity (10 min.) of particles having particle diameters of 300 to 150 μm is not less than 30 g/g under a load; and the single-layer absorption capacity (60 min.) of particles having particle diameters of 300 to 150 μm is not less than 30 g/g under a load.

It is necessary that the water-absorbent resin according to the present invention is surface-crosslinked with the surface-crosslinking agent including at least a polyhydric alcohol. If the water-absorbent resin is not surface-crosslinked in the above way, the blendability with fiber materials or shape-preserving ability is deteriorated when the water-absorbent resin is used for sanitary materials, there is a possibility that the water-absorbent resin displaying the following index of uniform surface-treatment cannot be obtained, and the absorption capacity is caused to lower when the water-absorbent resin is used as sanitary materials such as diapers.

It is necessary that the water-absorbent resin according to the present invention has a particle size distribution such that the ratio of particles having particle diameters of smaller than 150 μm is not more than 5 weight %. In case where the water-absorbent resin has a particle size distribution such that the ratio of particles having particle diameters of smaller than 150 μm is more than 5 weight %, an opening in absorbing materials is clogged with the particles having particle diameters of smaller than 150 μm when the water-absorbent resin is used as sanitary materials such as diapers. Therefore, liquids are inhibited from diffusing, and the properties of the product are caused to lower.

It is necessary that the water-absorbent resin according to the present invention exhibits an absorption capacity without a load of not less than 30 g/g. In case where the water-absorbent resin exhibits an absorption capacity without a load of less than 30 g/g, it is uneconomical because a large amount of the water-absorbent resin is necessary to obtain desirable absorption capacity when the water-absorbent resin is used as sanitary materials such as diapers.

When a water-absorbent resin is practically used for diapers, it is necessary that its particle each displays excellent capacities in order that the water-absorbent resin may realize excellent capacities. However, conventional measurement methods lack methods for estimating capacity of one of its particles.

For example, among the conventional measurement methods, the absorption capacity under a load described in the present specification was an estimate for the entirety of water-absorbent resin particles having a particle size distribution. Therefore, it is difficult to estimate capacities of each particle. In addition, even if the absorption capacity under a load was measured after adjustment of particle diameters (for example, in the range of 600 to 300 μm), the estimate was for a single particle diameter range (U.S. Pat. No. 5,147,343B1, EP 532002B1, and U.S. Pat. No. 5,601,542B1). Therefore, the surface-crosslinking state of the single particle diameter range could not be compared to that of other particle diameter ranges.

Furthermore, when the measurement of the absorption capacity under a load was carried out before, the amount of the water-absorbent resin as spread was much. Therefore, gels are in a tiering state after swelling, and a factor such as rearrangement of gels while swelling is included in addition to swellability of the water-absorbent resin under a load. In addition, vacancy liquid existing between the swollen gel particles, inhibits the estimate of the properties of the water-absorbent resin itself. In order to exclude this factor, the estimate, such that the amount as spread is adjusted in order that a gel layer can be single even after swelling, and then the vacancy liquid is removed, is a single-layer absorption capacity under a load. Its concrete measurement method is explained in the following examples.

The water-absorbent resin according to the present invention is preferably obtained by the production process for a water-absorbent resin according to the present invention. The production process is characterized in that: the treatment, preferably surface-crosslinking treatment of each water-absorbent resin particle is carried out highly uniformly. Therefore, the estimate represented by the single-layer absorption capacity under a load can exactly reflect capacities of the water-absorbent resin according to the present invention.

The water-absorbent resin, according to the present invention, is characterized in that: the single-layer absorption capacity (10 min.) of particles having particle diameters of 600 to 300 μm is not less than 30 g/g under a load; the single-layer absorption capacity (60 min.) of particles having particle diameters of 600 to 300 μm is not less than 30 g/g under a load; the single-layer absorption capacity (10 min.) of particles having particle diameters of 300 to 150 μm is not less than 30 g/g under a load; and the single-layer absorption capacity (60 min.) of particles having particle diameters of 300 to 150 µm is not less than 30 g/g under a load. The above-mentioned respective single-layer absorption capacities are preferably not less than 31 g/g under a load, more preferably not less than 32 g/g. In case where the above-mentioned respective single-layer absorption capacities are less than 30 g/g under a load, there are disadvantages in that the uniform treatment might not be carried out sufficiently.

The water-absorbent resin, according to the present invention, has a particle size distribution such that: the ratio of particles having particle diameters of 600 to 300 µm is preferably in the range of 65 to 85 weight %, more preferably 70 to 80 weight %; and the ratio of particles having particle diameters of 300 to 150 µM is preferably in the range of 10 to 30 weight %, more preferably 15 to 25 weight %.

In the water-absorbent resin according to the present invention, the time variation of the single-layer absorption capacity of particles having particle diameters of 600 to 300 µm under a load is preferably not less than 0.80.

Then, the time variation of the single-layer absorption capacity of particles having particle diameters of 600 to 300 µm under a load is calculated according to the following equation, and a value representing swellability under a load. This time variation is more preferably not less than 0.85, still more preferably not less than 0.90. That is to say, if the time variation is close to 1, there are advantages in reaching saturated swell in a short time.

Time variation of single-layer absorption capacity of particles having particle diameters of 600 to 300 µm under a load=(single-layer absorption capacity (10 min.) of particles having particle diameters of 600 to 300 µm under a load)/(single-layer absorption capacity (60 min.) of particles having particle diameters of 600 to 300 µm under a load).

In the water-absorbent resin according to the present invention, the time variation of the single-layer absorption capacity of particles having particle diameters of 300 to 150 µm under a load is preferably not less than 0.90.

Then, the time variation of the single-layer absorption capacity of particles having particle diameters of 300 to 150 µm under a load is calculated according to the following equation, and a value representing swellability under a load. This time variation is more preferably not less than 0.92, still more preferably not less than 0.95. That is to say, if the time variation is close to 1, there are advantages in reaching saturated swell in a short time.

Time variation of single-layer absorption capacity of particles having particle diameters of 300 to 150 µm under a load=(single-layer absorption capacity (10 min.) of particles having particle diameters of 300 to 150 µm under a load)/(single-layer absorption capacity (60 min.) of particles having particle diameters of 300 to 150 µm under a load).

In the water-absorbent resin according to the present invention, the variation between particles of the single-layer absorption capacity (10 min.) under a load is preferably in the range of 0.90 to 1.10.

Then, the variation between particles of the single-layer absorption capacity (10 min.) under a load is calculated according to the following equation, and a value representing uniformity of blending state. This variation between particles is more preferably in the range of 0.95 to 1.05, still more preferably 0.97 to 1.03.

Variation between particles of the single-layer absorption capacity (10 min.) under a load=(single-layer absorption capacity (10 min.) of particles having particle diameters of 300 to 150 µm under a load)/(single-layer absorption capacity (10 min.) of particles having particle diameters of 600 to 300 µM under a load).

In the water-absorbent resin according to the present invention, the variation between particles of the single-layer absorption capacity (60 min.) under a load is preferably in the range of not less than 0.90.

Then, the variation between particles of the single-layer absorption capacity (60 min.) under a load is calculated according to the following equation, and a value representing uniformity of blending state. This variation between particles is more preferably not less than 0.92, still more preferably not less than 0.95.

Variation between particles of the single-layer absorption capacity (60 min.) under a load=(single-layer absorption capacity (60 min.) of particles having particle diameters of 300 to 150 µm under a load)/(single-layer absorption capacity (60 min.) of particles having particle diameters of 600 to 300 µM under a load).

The water-absorbent resin, according to the present invention, is surface-crosslinked with a surface-crosslinking agent including at least a polyhydric alcohol, has a particle size distribution such that the ratio of particles having particle diameters of smaller than 150 µm is not more than 5 weight %, and exhibits an absorption capacity without a load of not less than 30 g/g, with the water-absorbent resin being characterized in that the index of uniform surface-treatment is not less than 0.70.

Then, the index of uniform surface-treatment is calculated according to the following equation, and a value enabling to exactly represent uniform surface-treatment. The index of uniform surface-treatment is preferably not less than 0.72, more preferably not less than 0.75, still more preferably not less than 0.80. If the index is close to 1, there are advantages in that the uniformity is enhanced.

Index of uniform surface-treatment=(time variation of single-layer absorption capacity of particles having particle diameters of 600 to 300 µm under a load)×(time variation of single-layer absorption capacity of particles having particle diameters of 300 to 150 µm under a load)×(variation between particles of the single-layer absorption capacity (10 min.) under a load)×(variation between particles of the single-layer absorption capacity (60 min.) under a load).

In the water-absorbent resin according to the present invention, the L value of light index measured with such as a spectrophotometer is preferably not less than 85, and the a value and b value representing chromaticness index are preferably in the range of −2 to 2, and 0 to 9 respectively. In case where the L, a, and b values is beyond these ranges, there are disadvantages in that the uniform treatment which is a characteristic of the present invention might not be carried out.

The water-absorbent resin, according to the present invention, can preferably be used as sanitary materials, such as disposable diapers, sanitary napkins, and incontinent pads due to its excellent properties, and provides the sanitary material according to the present invention.

Water-absorbent resins are generally produced or used as powders. Therefore, there was a problem such that the properties of the resultant sanitary material varied due to bias (segregation) of particle diameters of the powders, and the properties values were changed depending upon the absorption time. However, the present invention water-absorbent resin includes the polyhydric alcohol, and have higher properties (higher absorption capacity), and further, there is no difference of the properties between particle diameters or absorption times. Therefore, it is favorable when the water-absorbent resin is use as a sanitary material. When using the water-absorbent resin as a sanitary material, it was found that the properties values (single-layer absorption capacity under a load for a specific particle diameter or specific absorption time) of the present invention are critically important values. The present invention water-absorbent resin has higher properties, and can be used in higher resin concentration such that the core concentration defined by fiber material/water-absorbent resin is in the range of 30 to 100%, preferably 40 to 100%, more preferably 50 to 100%.

(Effects and Advantages of the Invention):

According to the present invention, the uniform blending of a water-absorbent resin with a liquid material, which is thought conventionally difficult because of the character such that the water-absorbent resin rapidly absorbs the liquid material when the water-absorbent resin comes into contact with the liquid material, can be carried out extremely easily and stably for a long time.

According to the present invention, the water-absorbent resin powder is efficiently and effectively allowed to react with the crosslinking agent. Therefore, there are advantages in view of industry and economy. The water-absorbent resin resultant from the surface-treatment of the water-absorbent resin powder in the above way has excellent absorption capacity and absorption capacity under a load.

Therefore, the water-absorbent resin resultant from the surface-treatment according to the present invention can fitly be used as water-absorbent resins for sanitary materials, such as disposable diapers and sanitary cotton, and besides, dew condensation inhibitors for building materials, water preserving agents for agriculture and gardening, or drying agent.

DETAILED DESCRIPTION OF THE PREFERRED EMBODIMENTS

Hereinafter, the present invention is more specifically illustrated by the following examples of some preferred embodiments in comparison with comparative examples not according to the invention. However, the present invention is not limited to the below-mentioned examples. Incidentally, absorption capacity without load and absorption capacity under a load are measured in the following way.

(a) Absorption capacity without load (merely referred as absorption capacity):

A nonwoven fabric bag (60 mm×60 mm), in which about 0.20 g of a water-absorbent resin was put uniformly, and was immersed into an aqueous sodium chloride solution of 0.9 wt % (physiological saline solution) at room temperature (25±2° C.). After 30 minutes, the bag was drawn up and then drained at 250×9.81 m/sec$^2$ (250 G) with a centrifuge for 3 minutes. Then, weight $W_1$ (g) of the bag was measured. In addition, the same procedure as the above was carried out using no water-absorbent resin, and weight $W_2$ (g) of the resultant bag was measured.

Thus, the absorption capacity (g/g) without load was calculated from these weights $W_1$ and $W_2$ in accordance with the following equation:

Absorption capacity (g/g) without load=(weight $W_1$ (g)−weight $W_2$ (g))/weight of water-absorbent resin (g).

(b) Absorption capacity under load (swollen liquid: physiological saline solution):

Hereinafter, when a physiological saline solution is used as a swollen liquid, a measurement apparatus as used for measuring the absorption capacity under a load is briefly explained while referring to FIG. 3.

Figure 3:
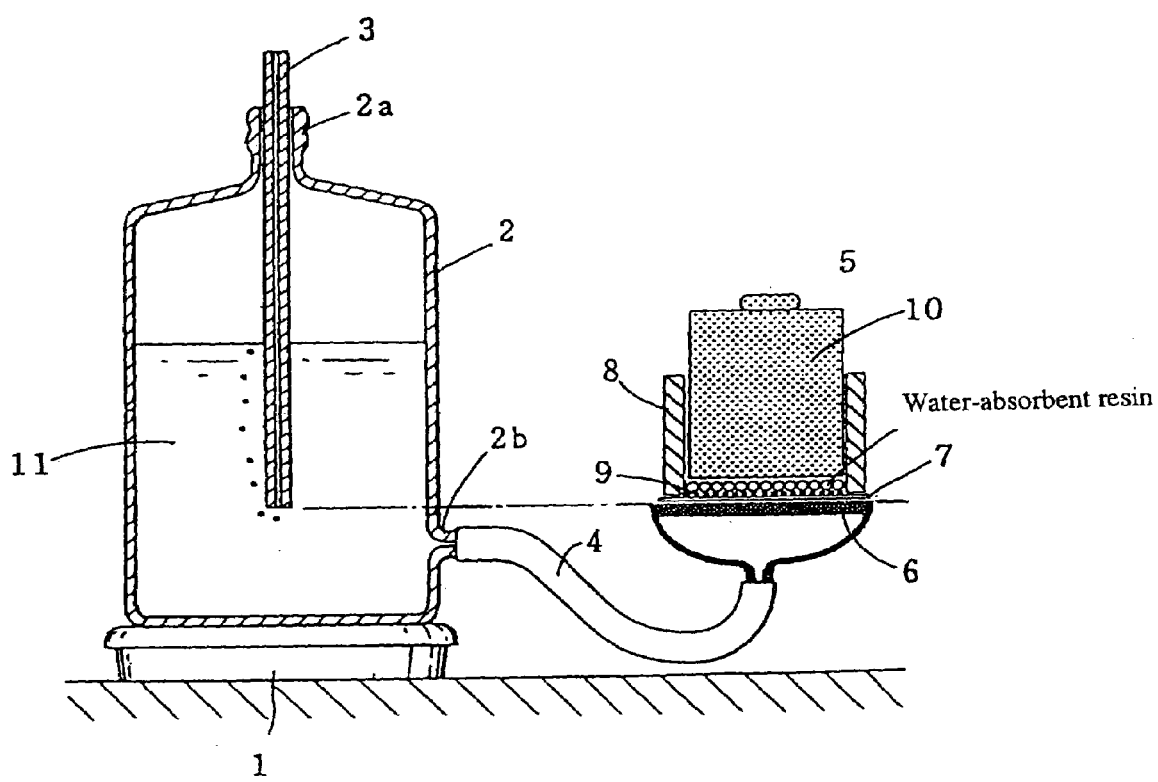
FIG. 3 is a schematic view of a measurement apparatus for measuring the water absorption capacity under a load, which is one of properties of water-absorbent resins in the present invention.

As is shown in FIG. 3, the measurement apparatus comprises: a balance 1; a vessel 2 of a predetermined capacity as mounted on the balance 1; an air-inhaling pipe 3; an introducing tube 4; a glass filter 6; and a measurement part 5 as mounted on this glass filter 6.

The vessel 2 has an opening part 2a on the top and an opening part 2b on the side, respectively. The air-inhaling pipe 3 is inserted in the opening part, and the introducing tube 4 is fitted to the opening part 2b. Incidentally, the vessel 2 contains a predetermined amount of an aqueous sodium chloride solution of 0.9 wt % (physiological saline solution, liquid temperature: 25±2° C.) 11.

In addition, the lower part of the air-inhaling pipe 3 is submerged in the physiological saline solution 11. The air-inhaling pipe 3 is fitted to keep the internal pressure of the vessel 2 almost atmospheric.

The glass filter 6 is formed in a diameter of 70 mm. The vessel 2 and the glass filter 6 are connected to each other through the introducing tube 4 made of a silicone resin. In addition, the position and the level of the glass filter 6 are fixed relative to the vessel 2. Furthermore, the glass filter 6 is fixed so that the position of the upper surface of the glass filter 6 would be slightly higher than the lower end of the air-inhaling pipe 3.

The measurement part 5 comprises: a filter paper 7; a supporting cylinder 8; a wire net 9 as attached to the bottom of the supporting cylinder 8; and a weight 10. The measurement part 5 is formed by mounting the filter paper 7 and the supporting cylinder 8, namely a wire net 9, in this order on the glass filter 6 and further mounting the weight 10 inside the supporting cylinder 8, namely on the wire net 9. The supporting cylinder 8 is formed in an internal diameter of 60 mm. The wire net 9 is made of stainless steel and formed in a mesh size of 38 μm (400 mesh). An arrangement is made such that a predetermined amount of water-absorbent resin can uniformly be spread on the wire net 9. In addition, the weight 10 is adjusted in weight such that a load of 20 g/cm$^2$ (about 1.96 kPa) can uniformly be applied to the water-absorbent resin.

The absorption capacity under a load was measured with the measurement apparatus having the above-mentioned constitution. The measurement method is hereinafter explained.

First, predetermined preparatory operations were made, in which, for example, a predetermined amount of the physiological saline solution 11 was placed into the vessel 2, and the air-inhaling pipe 3 was inserted into the vessel 2. Next, the filter paper 7 was mounted on the glass filter 6, and further. In parallel with this mounting operation, 0.900 g of water-absorbent resin was uniformly spread inside the supporting cylinder 8, namely, on the wire net 9, and the weight 10 was then put on this water-absorbent resin.

Then, the wire net 9 of the supporting cylinder 8, on which the water-absorbent resin and the weight 10 were put, was mounted on the filter paper 7 concentrically with the glass filter 6.

Then, the weight $W_3$ (g) of the physiological saline solution 11, as absorbed by the water-absorbent resin over a period of 60 minutes since the supporting cylinder 8 was mounted on the filter paper 7, was determined from a measured value with the balance 1.

Then, the absorption capacity (g/g) under the load in 60 minutes from the absorption initiation was calculated from the above-mentioned $W_3$ (g) and the weight of the water-absorbent resin (0.900 g) in accordance with the following equation.

Absorption capacity (g/g) under load=weight $W_3(g)$/ weight (g) of water-absorbent resin (c) Absorption capacity under load (swollen liquid: synthetic urine):

Hereinafter, when synthetic urine is used as a swollen liquid, a measurement apparatus as used for measuring the absorption capacity under a load is briefly explained while referring to FIG. 3.

As is shown in FIG. 3, the measurement apparatus comprises: a balance 1; a vessel 2 of a predetermined capacity as mounted on the balance 1; an air-inhaling pipe 3; an introducing tube 4; a glass filter 6; and a measurement part 5 as mounted on this glass filter 6. The vessel 2 has an opening part 2a on the top and an opening part 2b on the side, respectively. The air-inhaling pipe 3 is inserted in the opening part, and the introducing tube 4 is fitted to the opening part 2b. In addition, the vessel 2 contains a predetermined amount of synthetic urine 11. The lower part of the air-inhaling pipe 3 is submerged in the synthetic urine 11. The glass filter 6 is formed in a diameter of 70 mm. The vessel 2 and the glass filter 6 are connected to each other through the introducing tube. In addition, the upper portion of the glass filter 6 is fixed so that the position of the upper surface of the glass filter 6 would be slightly higher than the lower end of the air-inhaling pipe 3. The measurement part 5 comprises: a filter paper 7; a supporting cylinder 8; a wire net 9 as attached to the bottom of the supporting cylinder 8; and a weight 10. Then the measurement part 5 is formed by mounting the filter paper 7 and the supporting cylinder 8, namely a wire net 9, in this order on the glass filter 6 and further mounting the weight 10 inside the supporting cylinder 8, namely on the wire net 9. The supporting cylinder 8 is formed in an internal diameter of 60 mm. The wire net 9 is made of stainless steel and formed in a mesh size of 400 mesh (38 μm). An arrangement is made such that a predetermined amount of water-absorbent resin can uniformly be spread on the wire net 9. In addition, the weight 10 is adjusted in weight such that a load of 50 g/cm² (about 4.83 kPa) can uniformly be applied to the water-absorbent resin.

The absorption capacity under a load was measured with the measurement apparatus having the above-mentioned constitution. The measurement method is hereinafter explained.

First, predetermined preparatory operations were made, in which, for example, a predetermined amount of the synthetic urine 11 was placed into the vessel 2, and the air-inhaling pipe 3 was inserted into the vessel 2. Next, the filter paper 7 was mounted on the glass filter 6, and further. In parallel with this mounting operation, 0.900 g of water-absorbent resin was uniformly spread inside the supporting cylinder, namely, on the wire net 9, and the weight 10 was then put on this water-absorbent resin. Then, the wire net 9 of the supporting cylinder 8, on which the water-absorbent resin and the weight 10 were put was mounted.

Then, the weight $W_4$ (g) of the synthetic urine 11, as absorbed by the water-absorbent resin over a period of 60 minutes since the supporting cylinder 8 was mounted on the filter paper 7, was determined from a measured value with the balance 1.

Then, the absorption capacity (g/g) under the load in 60 minutes from the absorption initiation was calculated from the above-mentioned $W_4$ (g) in accordance with the following equation:

Absorption capacity (g/g) under load=weight $W_4(g)$/ weight (g) of water-absorbent resin The composition of the synthetic urine is shown in the following.

(sodium sulfate: 0.2 weight %, potassium chloride: 0.2 weight %, magnesium chloride 6 hydrate: 0.05 weight %, calcium chloride dihydrate: 0.025 weight %, ammonium dihydrogen phosphate: 0.085 weight %, diammonium hydrogen phosphate: 0.015 weight %, and deionized water: 99.425 weight %)

(d) Estimate of uniform surface-treatment:

A measurement apparatus as used for measuring the estimate of uniform surface-treatment is equal to that as used for measuring the absorption capacity under a load shown in FIG. 3

The estimate of uniform surface-treatment is carried out with this apparatus. Its measurement method is explained in the following.

First, predetermined preparatory operations were made, in which, for example, a predetermined amount of synthetic urine 11 (comprising: 0.2 weight % of sodium sulfate, 0.2 weight % of potassium chloride, 0.05 weight % of magnesium chloride 6 hydrate, 0.025 weight % of calcium chloride dihydrate, 0.085 weight % of ammonium dihydrogen phosphate, 0.015 weight % of diammonium hydrogen phosphate, and 99.425 weight % of deionized water, and liquid temperature: 25±2° C.) was placed into a vessel 2, and an air-inhaling pipe 3 was inserted into the vessel 2. Next, a filter paper 7 was mounted on a glass filter 6. In parallel with this mounting operation, 0.055±0.005 g of water-absorbent resin was uniformly spread inside a supporting cylinder 8, namely, on a wire net 9, and a weight 10 is then put on this water-absorbent resin. Thereafter, the total weight before measurement $W_5$ (g) of the supporting cylinder 8 fixed by the wire net 9, the water-absorbent resin, and the weight 10 was measured. Incidentally, as to the water-absorbent resin for measuring the estimate of uniform surface-treatment, water-absorbent resins having particle diameters of 600 to 300 μm and 300 to 150 μm respectively obtained by beforehand classification were used as measurement samples.

Then, the wire net 9 of the supporting cylinder 8, on which the water-absorbent resin and the weight 10 were put, was mounted on the filter paper 7 concentrically with the glass filter 6.

Then, the synthetic urine 11 was absorbed by the water-absorbent resin over a period of 10 or 60 minutes since the supporting cylinder 8 was mounted on the filter paper 7.

After a predetermined minute passed, the supporting cylinder 8 was softly transferred on five pieces of filter papers (made by Advantech Toyo, No. 2, diameter: 90 mm) as prepared beforehand while the load was applied to the water-absorbent resin without removing the weight 10, and vacancy liquid between the gelled water-absorbent resin particles as absorbed was drawn out for 2 minutes. The reason while the load was applied to the water-absorbent resin without removing the weight 10 in the above way and the vacancy liquid was drawn out is because the water-absorbent is inhibited from absorbing the vacancy liquid between the particles by lightening the weight.

Then, the total weight after measurement $W_6$ (g) of the supporting cylinder 8 fixed by the wire net 9, the water-absorbent resin, and the weight 10 was measured.

Then, the single-layer absorption capacity (g/g) under the load in 10 or 60 minutes from the absorption initiation was calculated from the above-mentioned $W_5$ g) and $W_6$ (g) in accordance with the following equation.

Single-layer absorption capacity (g/g) under load=
(total weight after measurement $W_6$(g)–total weight before measurement $W_5$(g))/weight (g) of water-absorbent resin Accordingly, the following four values of single-layer absorption capacities (g/g) under a load were calculated: the single-layer absorption capacity (10 min.) of particles having particle diameters of 600 to 300 μm under a load; the single-layer absorption capacity (60 min.) of particles having particle diameters of 600 to 300 μm under a load; the single-layer absorption capacity (10 min.) of particles having particle diameters of 300 to 150 μm under a load; and the single-layer absorption capacity (60 min.) of particles having particle diameters of 300 to 150μ under a load.

When the estimate of uniform surface-treatment was measured, the time variation of the single-layer absorption capacity under a load and the variation between particles of the single-layer absorption capacity under a load were further calculated.

The time variation of single-layer absorption capacity of particles having particle diameters of 600 to 300 μm under a load was calculated in accordance with the following equation.

Time variation of single-layer absorption capacity of particles having particle diameters of 600 to 300 μm under a load=(single-layer absorption capacity (10 min.) of particles having particle diameters of 600 to 300 μm under a load)/(single-layer absorption capacity (60 min.) of particles having particle diameters of 600 to 300 μm under a load).

The time variation of single-layer absorption capacity of particles having particle diameters of 300 to 150 μm under a load was calculated in accordance with the following equation.

Time variation of single-layer absorption capacity of particles having particle diameters of 300 to 150 μm under a load=(single-layer absorption capacity (10 min.) of particles having particle diameters of 300 to 150 μm under a load)/(single-layer absorption capacity (60 min.) of particles having particle diameters of 300 to 150 μm under a load).

The variation between particles of the single-layer absorption capacity (10 min.) under a load was calculated in accordance with the following equation.

Variation between particles of the single-layer absorption capacity (10 min.) under a load=(single-layer absorption capacity (10 min.) of particles having particle diameters of 300 to 150 μm under a load)/(single-layer absorption capacity (10 min.) of particles having particle diameters of 600 to 300 μm under a load).

The variation between particles of the single-layer absorption capacity (60 min.) under a load was calculated in accordance with the following equation.

Variation between particles of the single-layer absorption capacity (60 min.) under a load=(single-layer absorption capacity (60 min.) of particles having particle diameters of 300 to 150 μm under a load)/(single-layer absorption capacity (60 min.) of particles having particle diameters of 600 to 300 μm under a load).

Furthermore, the index of uniform surface-treatment was calculated from the four values of the variations as calculated in the above way in accordance with the following equation.

Index of uniform surface-treatment=(time variation of single-layer absorption capacity of particles having particle diameters of 600 to 300 μm under a load)×(time variation of single-layer absorption capacity of particles having particle diameters of 300 to 150 μm under a load)× (variation between particles of the single-layer absorption capacity(10 min.) under a load)× (variation between particles of the single-layer absorption capacity (60 min.) under a load).

EXAMPLE 1

In a kneader equipped with two sigma type blades, an aqueous acrylic acid salt monomer solution having a monomer concentration of 38 weight % and a neutralization ratio of 75 mol % was prepared, wherein the aqueous monomer solution comprised an aqueous sodium acrylate solution, acrylic acid and water. Trimethylolpropane triacrylate as an internal-crosslinking agent was dissolved therein so that its concentration would be adjusted to 0.02 mol % of the monomer. Next, the amount of dissolved oxygen of the aqueous monomer solution was decreased and the entirety of the reaction apparatus was replaced with nitrogen gas by introducing the nitrogen gas into the aqueous solution. Next, while the two sigma blades were rotated, 0.05 mol % of sodium persulfate and 0.0003 mol % of L-ascorbic acid were added as a polymerization initiator to carry out a stirring polymerization in the kneader, thus obtaining a hydrogel polymer having an average particle diameter of about 2 mm after 40 minutes.

The resultant hydrogel polymer was dried in a hot air dryer adjusted at a temperature of 170° C. for 60 minutes. The resultant dried product was pulverized with a roller mill, and then classified with a mesh of 850 μm to remove particles larger than 850 μm, thus obtaining a water-absorbent resin (A1).

The above water-absorbent resin (A1) was kept at about 60° C. and supplied into a continuous high-speed-stirring blender (a turbulizer made by Hosokawa Micron Co., Ltd.) equipped with two hydraulic hollow cone spray nozzles (C1, 1/4M-K-040, made by H. Ikeuchi & Co., Ltd.; their spray patterns were circular and hollow cone shapes) with a feeding speed of 100 kg/hr, and an aqueous surface-crosslinking agent solution prepared with a blending ratio of glycerin water:isopropyl alcohol=1:4:1 as a liquid material (B1) was blended therewith by spraying so that the amount of the aqueous solution as added would be adjusted to 3 weight % relative to the weight of the water-absorbent resin (A1). After the resultant mixture was heat-treated at a water-absorbent resin temperature (material temperature) of 190° C. for one hour, the entirety was passed through a sieve having a mesh opening of 850 μm, thus obtaining a surface-treated water-absorbent resin (1).

The hydraulic hollow cone spray nozzles (C1, 1/4M-K-040) were used. Therefore, the spray angle of the aqueous surface-treating agent solution from the hydraulic hollow cone spray nozzles was 70°, and the dispersing area of a spray-dispersing state projected onto a sectional area perpendicular to the stirring shaft direction of the blending apparatus accounted for about 89% by the nozzles.

After finishing the above procedure, the internal portion of the blender was observed. Then, large piled materials were observed little.

The properties of the resultant surface-treated water-absorbent resin (1) were listed in Table 1.

EXAMPLE 2

A surface-treated water-absorbent resin (2) was obtained in the same way as of Example 1 except that the blender was changed into a continuous high-speed-stirring blender equipped with two hydraulic flat spray nozzles (C2, 1/4M-V-115-05, made by H. Ikeuchi & Co., Ltd.; their spray patterns were double-convex-lens and elliptic cone shapes). Incidentally, the hydraulic flat spray nozzles (C2, 1/4M-V-115-05) were attached to the blender very carefully so that the spray angle would be the largest when the dispersing area of a spray-dispersing state was projected onto a sectional area perpendicular to the stirring shaft direction of the continuous high-speed-stirring blending apparatus.

The spray angle was 110° by use of the hydraulic flat spray nozzles (C2, 1/4M-V-115-05) when the dispersing area of a spray-dispersing state was projected onto a sectional area perpendicular to the stirring shaft direction of the blending apparatus. The dispersing area of a spray-dispersing state projected onto a sectional area perpendicular to the shaft direction of the blending apparatus accounted for about 97% by the nozzles.

After finishing the above procedure, the internal portion of the blender was observed. Then, large piled materials were observed little.

The properties of the resultant surface-treated water-absorbent resin (2) were listed in Table 1.

EXAMPLE 3

A surface-treated water-absorbent resin (3) was obtained in the same way as of Example 1 except that the blender was changed into a continuous high-speed-stirring blender equipped with a hydraulic hollow cone spray nozzle (C3, 1/4M-K-100, made by H. Ikeuchi & Co., Ltd.; its spray pattern was a circular and hollow cone shape (a hollow cone spray shape)).

The hydraulic hollow cone spray nozzle (C3, 1/4M-K-100) was used. Therefore, the spray angle of the aqueous surface-treating agent solution from the hydraulic hollow cone spray nozzle was 70°, and the dispersing area of a spray-dispersing state projected onto a sectional area perpendicular to the shaft direction of the blending apparatus accounted for about 77%.

After finishing the above procedure, the internal portion of the blender was observed. Then, large piled materials were observed little.

The properties of the resultant surface-treated water-absorbent resin (3) were listed in Table 1.

COMPARATIVE EXAMPLE 1

A comparative surface-treated water-absorbent resin (1) was obtained in the same way as of Example 1 except that the blender was changed into a continuous high-speed-stirring blender equipped with two straight pipe nozzles (C1') having an internal diameter of 6 mm in stead of the hydraulic hollow cone spray nozzles made by H. Ikeuchi & Co., Ltd.

The aqueous surface-crosslinking agent solution (B1) was supplied in a form of liquid drop from the straight pipe nozzles (C1') as used. Therefore, the spray angle and the dispersing area of a spray-dispersing state projected onto a sectional area of the blending apparatus could not be measured.

After finishing the above procedure, the internal portion of the blender was observed. Then, the growth of piled materials was partially observed on the stirring paddle.

The resultant comparative surface-treated water-absorbent resin (1) had particles which were agglomerated rigidly, and could not be crashed, and weren't passed through a sieve having a mesh opening of 850 µm. Therefore, the properties of the resultant comparative surface-treated water-absorbent resin (1) were listed in Table 1. However, the value of the particle size distribution as measured includes particles not passing through a sieve having a mesh opening of 850 µm. The absorption capacity without load and absorption capacity under a load were measured by removing the particles not passing through a sieve having a mesh opening of 850 µm.

COMPARATIVE EXAMPLE 2

A comparative surface-treated water-absorbent resin (2) was obtained in the same way as of Example 1 except that the blender was changed into a continuous high-speed-stirring blender equipped with an air-atomizing nozzle (C2', its spray setup number was SU1, and its spray pattern was a circular and full cone shape; made by Spraying Systems Co., Japan).

The air-atomizing nozzle (C2', its spray setup number was SU1, made by Spraying Systems Co., Japan) was used. Therefore, the spray angle of the aqueous surface-treating agent solution from the air-atomizing nozzle was 18°, and the dispersing area of a spray-dispersing state projected onto a sectional area perpendicular to the shaft direction of the blending apparatus accounted for about 20%.

After finishing the above procedure, the internal portion of the blender was observed. Then, piled materials were observed on the stirring paddle and shaft.

The resultant comparative surface-treated water-absorbent resin (2) had particles which were agglomerated rigidly, and could not be crashed, and weren't passed through a sieve having a mesh opening of 850 µm. Therefore, the properties of the resultant comparative surface-treated water-absorbent resin (2) were listed in Table 1. However, the value of the particle size distribution as measured includes particles not passing through a sieve having a mesh opening of 850 µm. The absorption capacity without load and absorption capacity under a load were measured by removing the particles not passing through a sieve having a mesh opening of 850 µm.

EXAMPLE 4

The granulation was carried out in order to decrease the amount of the surface-treated water-absorbent resin (1) as passed through a sieve having a mesh opening of 150 µm. That is to say, the water-absorbent resin (1) as a water-absorbent resin (A2) before modifying was supplied into a continuous high-speed-stirring blender (a turbulizer made by Hosokawa Micron Co., Ltd.) equipped with two hydraulic hollow cone spray nozzles (C1, 1/4M-K-040, made by H. Ikeuchi & Co., Ltd.; their spray patterns were circular and hollow cone shapes) with a feeding speed of 100 kg/hr, and water as a liquid material (B4) was blended therewith so that the amount of the water as added would be adjusted to 5 weight % relative to the weight of the water-absorbent resin (A2). Then, the resultant mixture was left still at 80° C. for 1 hour to cure, and the entirety was passed through a sieve having a mesh opening of 850 µm, thus obtaining a modified (granulated) water-absorbent resin (4).

The hydraulic hollow cone spray nozzles (C1, 1/4M-K-040) were used. Therefore, the spray angle of the water (B4)

was 70°, and the dispersing area of a spray-dispersing state projected onto a sectional area of the blending apparatus accounted for about 89% by the nozzles.

After finishing the above procedure, the internal portion of the blender was observed. Then, large piled materials were observed little.

The properties of the resultant modified (granulated) water-absorbent resin (4) were listed in Table 2.

EXAMPLE 5

A modified (granulated) water-absorbent resin (5) was obtained in the same way as of Example 4 except that the blender was changed into a continuous high-speed-stirring blender equipped with two hydraulic flat spray nozzles (C2, 1/4M-V-115-05, made by H. Ikeuchi & Co., Ltd.; their spray patterns were double-convex-lens and elliptic cone shapes). Incidentally, the hydraulic flat spray nozzles (C2, 1/4M-V-115-05) were attached to the blender very carefully so that the spray angle would be the largest when the dispersing area of a spray-dispersing state was projected onto a sectional area perpendicular to the stirring shaft direction of the continuous high-speed-stirring blending apparatus.

The hydraulic flat spray nozzles (C2, 1/4M-V-115-05) were used. Therefore, the spray angle was 110°, and the dispersing area of a spray-dispersing state projected onto a sectional area of the blending apparatus accounted for about 97% by the nozzles.

After finishing the above procedure, the internal portion of the blender was observed. Then, large piled materials were observed little.

The properties of the resultant modified (granulated) water-absorbent resin (5) were listed in Table 2.

EXAMPLE 6

A modified (granulated) water-absorbent resin (6) was obtained in the same way as of Example 4 except that the blender was changed into a continuous high-speed-stirring blender equipped with a hydraulic hollow cone spray nozzle (C3, 1/4M-K-100, made by H. Ikeuchi & Co., Ltd.; its spray pattern was a circular and hollow cone shape (a hollow cone spray shape)).

The hydraulic hollow cone spray nozzle (C3, 1/4M-K-100) was used. Therefore, the spray angle of the water (B4) was 70°, and the dispersing area of a spray-dispersing state projected onto a sectional area of the blending apparatus accounted for about 77%.

After finishing the above procedure, the internal portion of the blender was observed. Then, large piled materials were observed little.

The properties of the resultant modified (granulated) water-absorbent resin (6) were listed in Table 2.

COMPARATIVE EXAMPLE 3

A comparative modified (granulated) water-absorbent resin (3) was obtained in the same way as of Example 4 except that the blender was changed into a continuous high-speed-stirring blender equipped with two hydraulic flat spray nozzles (C3', 1/4M-V-040-05, made by H. Ikeuchi & Co., Ltd.; their spray patterns were double-convex-lens and elliptic cone shapes). Incidentally, the hydraulic flat spray nozzles (C3', 1/4M-V-040-05) were attached to the blender very carefully so that the spray angle would be the largest when the dispersing area of a spray-dispersing state was projected onto a sectional area perpendicular to the stirring shaft direction of the continuous high-speed-stirring blending apparatus.

The spray angle was 40° by use of the hydraulic flat spray nozzles (C3', 1/4M-V-040-05) when the dispersing area of a spray-dispersing state was projected onto a sectional area perpendicular to the stirring shaft direction of the blending apparatus. The dispersing area of a spray-dispersing state projected onto a sectional area perpendicular to the shaft direction of the blending apparatus accounted for about 67% by the nozzles.

After finishing the above procedure, the internal portion of the blender was observed. Then, piled materials were observed on the stirring paddle and shaft.

The resultant comparative modified (granulated) water-absorbent resin (3) had particles which were agglomerated rigidly, and could not be crashed, and weren't passed through a sieve having a mesh opening of 850 μm. Therefore, the properties of the resultant comparative water-absorbent resin (3) were listed in Table 2. However, the value of the particle size distribution as measured includes particles not passing through a sieve having a mesh opening of 850 μm.

COMPARATIVE EXAMPLE 4

A comparative modified (granulated) water-absorbent resin (4) was obtained in the same way as of Example 4 except that the blender was changed into a continuous high-speed-stirring blender equipped with two hydraulic flat spray nozzles (C2, 1/4M-V-115-05, made by H. Ikeuchi & Co., Ltd.; their spray patterns were double-convex-lens and elliptic cone shapes). Incidentally, the hydraulic flat spray nozzles (C2, 1/4M-V-115-05) were attached to the blender very carefully so that the spray angle would be the smallest when the dispersing area of a spray-dispersing state was projected onto a sectional area perpendicular to the stirring shaft direction of the continuous high-speed-stirring blending apparatus.

When the hydraulic flat spray nozzles (C2, 1/4M-V-115-05) were used, they were attached carefully so that the spray angle would be the smallest in the above way. Therefore, the spray angle was 10° when the dispersing area of a spray-dispersing state was projected onto a sectional area perpendicular to the stirring shaft direction of the blending apparatus. The dispersing area of a spray-dispersing state projected onto a sectional area of the blending apparatus accounted for about 23% by the nozzles.

After finishing the above procedure, the internal portion of the blender was observed. Then, piled materials were observed on the stirring paddle and shaft.

The resultant comparative modified (granulated) water-absorbent resin (4) had particles which were agglomerated rigidly, and could not be crashed, and weren't passed through a sieve having a mesh opening of 850 μm. Therefore, the properties of the resultant comparative water-absorbent resin (4) were listed in Table 2. However, the value of the particle size distribution as measured includes particles not passing through a sieve having a sieve opening of 850 μm.

TABLE 1

|  |  | Example 1 | Example 2 | Example 3 | Comparative Example 1 | Comparative Example 2 |
|---|---|---|---|---|---|---|
| Absorption capacity without a load (g/g) | | 34.3 | 35.1 | 35.3 | 34.9 | 34.7 |
| Absorption capacity under a load (g/g) | | 27.7 | 27.5 | 27.0 | 23.2 | 24.9 |
| Particle size distribution | Not smaller than 850 μm | 0.0 | 0.0 | 0.0 | 0.9 | 0.8 |
| | 850 to 500 μm | 29.7 | 29.4 | 29.1 | 30.0 | 29.1 |
| | 500 to 300 μm | 45.0 | 44.7 | 45.7 | 43.5 | 44.5 |
| | 300 to 150 μm | 19.3 | 19.7 | 18.9 | 18.5 | 18.2 |
| | Smaller than 150 μm | 6.0 | 6.2 | 6.3 | 7.1 | 7.4 |

The absorption capacity under a load was measured by use of a physiological saline solution as a swollen liquid.

TABLE 2

|  |  | Example 4 | Example 5 | Example 6 | Comparative Example 3 | Comparative Example 4 |
|---|---|---|---|---|---|---|
| Particle size distribution | Not smaller than 850 μm | 0.0 | 0.0 | 0.0 | 1.2 | 1.8 |
| | 850 to 500 μm | 33.3 | 32.9 | 32.2 | 32.0 | 31.5 |
| | 500 to 300 μm | 46.4 | 46.1 | 45.5 | 45.3 | 45.5 |
| | 300 to 150 μm | 16.4 | 17.7 | 17.8 | 16.3 | 15.7 |
| | Smaller than 150 μm | 3.9 | 3.3 | 4.5 | 5.2 | 5.5 |

From Table 1, the resultant surface-crosslinked water-absorbent resin obtained by blending according to the present invention process displayed a higher absorption capacity under a load, and was not observed to produce very hard agglomerated materials such that could not be passed through a sieve having a mesh opening of 850 μm in comparison with those obtained by a blending process using the straight pipe nozzles. In addition, it would be understood that: the growth of piled materials due to adding the liquid material excessively was not observed in the blending apparatus, and the water-absorbent resin was uniformly blended with the aqueous surface-crosslinking agent solution as the liquid material.

From Table 2, the ratio of particles smaller than 150 μm was decreased, and the production of very hard agglomerated materials such that could not be passed through a sieve having a mesh opening of 850 μm was not observed, because the blending process according to the present invention was applied. It would be understood that the present process was effective for blending much aqueous solution for the purpose of decreasing dusts of water-absorbent resins as caused.

From the above results, the blending process according to the present invention can be regarded as a very effective process for water-absorbent resins easily agglomerated by blending with a liquid material when the uniform blending state is required.

REFERENTIAL EXAMPLE 1

An aqueous monomer solution was prepared by mixing 3,683 parts by weight of aqueous sodium acrylate solution of 37 weight %, 562 parts by weight of acrylic acid, 4.26 parts by weight of polyethylene glycol diacrylate (average unit of ethylene oxide: 8), and 1,244 parts by weight of deionized water. In a monomer degassing vessel, nitrogen was blown into 1 liter of this aqueous monomer solution with a feeding rate of 0.8 liter/minute for 30 minutes in order to remove the dissolved oxygen in the aqueous solution. Next, 4.5 parts by weight of an aqueous sodium perfulfate solution of 5 weight %, 4.0 part by weight of an aqueous L-ascorbic acid solution of 0.5 weight %, and 4.4 parts by weight of 2,2'-azobis-(2-amidinopropane)dihydrochloride solution were mixed with the aqueous monomer solution from a polymerization initiator vessel respectively. While 3.2 parts by weight of an aqueous hydrogen peroxide solution of 3.5 weight % was supplied, the aqueous monomer solution mixed with the polymerization initiator was supplied onto a belt to carry out a stationary polymerization continuously.

The full length of the belt was 3.5 m, and the interval from a portion for supplying the aqueous monomer solution to 1 m toward the driving direction was equipped with a cooling apparatus for cooling the surface of the belt, and the residual portion was equipped with a heat-treating apparatus for heating the surface of the belt. The aqueous monomer solution supplied onto the belt formed a viscous gel material after about one minute, and the temperature was reached to the maximum after 7 minutes. The maximum temperature was 80° C. Continuously, the polymerized gel was matured in a heating zone of 60° C., thus obtaining a transparent hydrogel. This hydrogel was crushed with a meat chopper, and dried in a hot-blow dryer for 65 minutes at 160° C. The resultant dried product was crushed, thus obtaining a water-absorbent resin (A3) having an average particle diameter of 350 μm, wherein particles having particle diameters of smaller than 150 μm was 5 weight % of the water-absorbent resin. Its absorption capacity and extractable content were 52 times (52 g/g) and 12% respectively.

EXAMPLE 7

A mixed composition comprising 0.5 part of 1,3-propanediol, 0.5 part of propylene glycol, 3.0 parts of water, and 0.5 part of ethanol was blended into 100 parts of the water-absorbent resin (A3) as obtained in Referential Example 1 with a turbulizer. The mixture as obtained was heat-treated for one hour in a paddle-type dryer, wherein the internal wall (heat medium) temperature of the paddle-type dryer was 185° C., and the atmosphere of the space portion in the dryer was adjusted to have a dew point of 40° C. and a temperature of 97° C., thus obtaining a water-absorbent resin (absorbing agent) (7). The results were listed in Table 3.

EXAMPLE 8

A water-absorbent resin (absorbing agent) (8) was obtained in the same way as of Example 7 except that the atmosphere of the space portion in the paddle-type dryer was adjusted to have a dew point of 50° C. and a temperature of 119° C. The results were listed in Table 3.

EXAMPLE 9

A mixed composition comprising 0.5 part of 1,3-propanediol, 0.5 part of propylene glycol, 3.0 parts of water, and 0.5 part of ethanol was blended into 100 parts of the water-absorbent resin (A3) as obtained in Referential Example 1 with a turbulizer. The mixture as obtained was heat-treated for one hour in a double-arm type kneader, wherein the internal wall (heat medium) temperature of the double-arm type kneader was 185° C., and the atmosphere of the space portion in the dryer was adjusted to have a dew point of 60° C. and a temperature of 145° C., thus obtaining a water-absorbent (absorbing agent) (9). The results were listed in Table 3.

COMPARATIVE EXAMPLE 5

A comparative water-absorbent resin (comparative absorbing agent) (5) was obtained in the same way as of Example 7 except that the atmosphere of the space portion in the paddle-type dryer was adjusted to have a dew point of 25° C. and a temperature of 88° C. The results were listed in Table 3.

COMPARATIVE EXAMPLE 6

A comparative water-absorbent resin (comparative absorbing agent) (6) was obtained in the same way as of Example 7 except that the atmosphere of the space portion in the paddle-type dryer was adjusted to have a dew point of 100° C. and a temperature of 142° C. The results were listed in Table 3.

of 75 mol % was prepared, wherein the aqueous monomer solution comprised an aqueous sodium acrylate solution, acrylic acid and water. Polyethylene glycol diacrylate (average ethylene oxide unit: 8) as an internal-crosslinking agent was dissolved therein so that its concentration would be adjusted to 0.035 mol % of the monomer. Next, the amount of dissolved oxygen of the aqueous monomer solution was decreased and the entirety of the reaction apparatus was replaced with nitrogen gas by introducing the nitrogen gas into the aqueous solution. Next, while the two sigma blades were rotated, 0.05 mol % of sodium persulfate and 0.0003 mol % of L-ascorbic acid were added as a polymerization initiator to carry out a stirring polymerization in the kneader, thus obtaining a hydrogel polymer having an average particle diameter of about 2 mm after 40 minutes.

The resultant hydrogel polymer was dried in a hot air dryer adjusted at a temperature of 170° C. for 60 minutes. The resultant dried product was pulverized with a roller mill, and then classified with a mesh of 850 μm to remove particles larger than 850 μm, thus obtaining a water-absorbent resin (A4). The resultant water-absorbent resin (A4) had a particle size distribution such that the average particle diameter was 350 μm and the ratio of particles having particle diameters of smaller than 150 μm was 7 weight %, and exhibited an absorption capacity of 45 times (45 g/g).

The above water-absorbent resin (A4) was supplied into a continuous high-speed-stirring blender (a turbulizer made by Hosokawa Micron Co., Ltd.) equipped with a hydraulic hollow cone spray nozzle (C1, 1/4M-K-040, made by H. Ikeuchi & Co., Ltd.; its spray pattern was a circular and hollow cone shape) with a feeding speed of 100 kg/hr, and an aqueous surface-crosslinking agent solution prepared with a blending ratio of 1,4-butandiol: propylene glycol: water=1:1:6 as a liquid material (B10) was blended therewith so that the amount of the aqueous solution as added would be adjusted to 4 weight % relative to the weight of the water-absorbent resin (A4). After the resultant mixture was heat-treated for 50 minutes in a paddle-type dryer of 190° C. (water-absorbent resin temperature (material temperature)),

TABLE 3

| | | Atmosphere | | Absorption | Absorption |
| --- | --- | --- | --- | --- | --- |
| | | Dew point (° C.) | Temperature (° C.) | capacity (g/g) | capacity under a load (g/g) |
| Example 7 | Water-absorbent resin (absorbing agent) (7) | 40 | 97 | 35 | 32 |
| Example 8 | Water-absorbent resin (absorbing agent) (8) | 50 | 119 | 33 | 35 |
| Example 9 | Water-absorbent resin (absorbing agent) (9) | 60 | 145 | 35 | 30 |
| Comparative Example 5 | Comparative water-absorbent resin (comparative absorbing agent) (5) | 25 | 88 | 40 | 14 |
| Comparative Example 6 | Comparative water-absorbent resin (comparative absorbing agent) (6) | 100 | 142 | 37 | 13 |

The absorption capacity under a load was measured by use of synthetic urine as a swollen liquid.

EXAMPLE 10

In a kneader equipped with two sigma type blades, an aqueous acrylic acid salt monomer solution having a monomer concentration of 38 weight % and a neutralization ratio wherein the atmosphere of the upper space inside of the paddle-type dryer had a dew point of 50° C. and a temperature of 160° C., the entirety was passed through a sieve having a mesh opening of 850 μm, thus obtaining a surface-treated water-absorbent resin (10).

The hydraulic hollow cone spray nozzle (C1, 1/4M-K-040; its spray pattern was a circular and hollow cone shape) was used. Therefore, the spray angle of the aqueous surface-treating agent solution from the hydraulic hollow cone spray nozzle was 70°, and the dispersing area of a spray-dispersing state projected onto a sectional area perpendicular to the stirring shaft direction of the blending apparatus accounted for about 77%.

After finishing the above procedure, the internal portion of the blender was observed. Then, large piled materials were observed little.

The properties of the resultant surface-treated water-absorbent resin (10) were listed in Table 4.

EXAMPLE 11

All the procedures were carried out in the same way as of Example 10 except that the aqueous surface-crosslinking agent solution was replaced with an aqueous surface-crosslinking agent solution (B11) prepared with a blending ratio of 1,3-dioxolane-2-one:water:ethanol=1:1:1 as the liquid material, and was blended so that the amount of the aqueous solution as added would be adjusted to 7.5 weight % relative to the weight of the water-absorbent resin (A4).

The properties of the resultant water-absorbent resin (11) were listed in Table 4.

As is shown in Table 4, when the polyhydric alcohol was not used, the properties of Example 11 were inferior to that of Example 10. Incidentally, Example 11 is an example for the production process, but is not for the water-absorbent resin.

EXAMPLE 12

All the procedures were carried out in the same way as of Example 10 except that the mixture resultant from the water-absorbent resin (A4) and the liquid material (B10) was heat-treated for 50 minutes in a paddle-type dryer of 190° C. (water-absorbent resin temperature (material temperature)), wherein the atmosphere of the upper space inside of the paddle-type dryer had a dew point of 40° C. and a temperature of 80° C.

The properties of the resultant water-absorbent resin (12) were listed in Table 4.

As is shown in Table 4, the properties of Example 12 were inferior to that of Example 10. Incidentally, Example 12 is an example for the production process, but is not for the water-absorbent resin.

illustration only, and not for the purpose of limiting the invention as defined by the appended claims and their equivalents.

What is claimed is:

1. A water-absorbent resin, which is surface-crosslinked with a surface-crosslinking agent including at least a polyhydric alcohol, wherein the water-absorbent resin before surface-crosslinking is obtained by polymerizing hydrophilic monomers comprising a major proportion of either or both of acrylic acid and its salt (neutralized product), and where the water-absorbent resin has a particle size distribution such that the ratio of particles having particle diameters of smaller than 150 μm is not more than 5 weight %, and exhibits an absorption capacity without a load of not less than 30 g/g, with the water-absorbent resin being characterized in that:
a single-layer absorption capacity (10 min.) of particles having particle diameters of 600 to 300 μm is not less than 30 g/g under a load; the single-layer absorption capacity (60 min.) of particles having particle diameters of 600 to 300 μm is not less than 30 g/g under a load; the single-layer absorption capacity (10 min.) of particles having particle diameters of 300 to 150 μm is not less than 30 g/g under a load; and the single-layer absorption capacity (60 min.) of particles having particle diameters of 300 to 150 μm is not less than 30 g/g under a load, wherein the single-layer absorption capacity is measured under the following conditions:

(a) the liquid being absorbed is a synthetic urine (comprising 0.2 weight % of sodium sulfate, 0.2 weight % of potassium chloride, 0.05 weight % of magnesium chloride 6 hydrates, 0.025 weight % of calcium chloride dihydrate, 0.085 weight % of ammonium dihydrogen phosphate, 0.015 weight % of diammonium hydrogen phosphate, and 99.425 weight % of deionized water) at 25±2° C., (b) the load applied to the measurement sample during the absorption is 50 g/cm² (4.83 kPa).

(c) the amount of the water-absorbent resin as a measurement sample is 0.055±0.005 g, and (d) the water-absorbent resin as a measurement sample is uniformly spread on the wire net made of stainless steel attached to the bottom of the cylinder having an internal diameter of 60 mm, wherein the absorption capacity without a load is measured with a sample drained with a centrifuge after

TABLE 4

| | | | Example 10 | Example 11 | Example 12 |
|---|---|---|---|---|---|
| Single-layer | 600 to 300 μm | 10 min. | 31.8 | 29.2 | 32.0 |
| absorption capacity | | 60 min. | 37.9 | 37.2 | 39.6 |
| under a load (g/g) | 300 to 150 μm | 10 min. | 32.2 | 30.3 | 29.8 |
| | | 60 min. | 34.3 | 32.3 | 33.9 |
| Time variation of single-layer absorption | 600 to 300 μm | | 0.84 | 0.78 | 0.81 |
| capacity under a load | 300 to 150 μm | | 0.94 | 0.94 | 0.88 |
| Variation between particles of single-layer | 10 min. | | 1.01 | 1.03 | 0.93 |
| absorption capacity under a load | 60 min. | | 0.91 | 0.87 | 0.87 |
| Index of uniform surface-treatment | | | 0.73 | 0.66 | 0.58 |
| Absorption capacity (g/g) | | | 34 | 32 | 34 |

Various details of the invention may be changed without departing from its spirit not its scope. Furthermore, the foregoing description of the preferred embodiments according to the present invention is provided for the purpose of immersed into an aqueous sodium chloride solution of 0.9 weight % for 30 minutes.

2. A water-absorbent resin according to claim 1, having a particle size distribution such that the ratio of parties having particle diameters of 600 to 300 μm is in the range of 65 to 85 weight %, and the ratio of particles having particle diameters of 300 to 150 μm is in the range of 10 to 30 weight %, where the particle size distribution is measured by a classification using a sieve.

3. A water-absorbent resin according to claim 1, having an L value of light index measured with a spectrophotometer of not less than 85, and the a value representing chromaticness index of in the range of −2 to 2 and the b value representing chromaticness index of in the range of 0 to 9.

4. A sanitary material, comprising a water-absorbent resin and a fiber material,
wherein the water-absorbent resin is according to claim 1, and has a particle size distribution such that the ratio of particles having particles diameters of 600 to 300 μm is in the range of 65 to 85 weight %, and the ratio of particles having particle diameters of 300 to 150 μm is in the range of 10 to 30 weight %.

5. A water-absorbent resin, which is surface-crosslinked with a surface-crosslinking agent including at least a polyhydric alcohol, wherein the water-absorbent resin before surface-crosslinking is obtained by polymerizing hydrophilic monomers comprising a major proportion of either or both of acrylic acid and its salt (neutralized product), and where the water-absorbent resin has a particle size distribution such that the ratio of particles having particle diameters of smaller than 150 μm is not more than 5 weight %, and exhibits an absorption capacity without a load of not less than 30 g/g,
with the water-absorbent resin being characterized in that the index of uniform surface-treatment is not less than 0.70,
wherein: index of uniform surface-treatment=(time variation of single-layer absorption capacity of particles having particle diameters of 600 to 300 μm under a load)×(time variation of single-layer absorption capacity of particles having particle diameters of 300 to 150 μm under a load)×(variation between particles of the single-layer absorption capacity (10 min.) under a load)×(variation between particles of the single-layer absorption capacity (60 min.) under a load),
where: time variation of single-layer absorption capacity of particles having particle diameters of 600 to 300 μm under a load=(single-layer absorption capacity (10 min.) of particles having particle diameters of 600 to 300 μm under a load)/(single-layer absorption capacity (60 min.) of particles having particle diameters of 600 to 300 μm under a load); time variation of single-layer absorption capacity of particles having particle diameters of 300 to 150 μm under a load=(single-layer absorption capacity (10 min.) of particles having particle diameters of 300 to 150 μm under a load)/(single-layer absorption capacity (60 min.) of particles having particle diameters of 300 to 150 μm under a load); variation between particles of the single-layer absorption capacity (10 min.) under a load=(single-layer absorption capacity (10 min.) of particles having particle diameters of 300 to 150 μm under a load)/(single-layer absorption capacity (10 min.) of particles having particle diameters of 600 to 300 μm under a load): and variation between particles of the single-layer absorption capacity (60 min.) under a load=(single-layer absorption capacity (60 min.) of particles having particle diameters of 300 to 150 μm under a load)/(single-layer absorption capacity (60 min.) of particles having particle diameters of 600 to 300 μm under a load);
wherein the single-layer absorption capacity is measured under the following conditions:
(a) the liquid being absorbed is a synthetic urine (comprising 0.2 weight % of sodium sulfate, 0.2 weight % of potassium chloride, 0.05 weight % of magnesium chloride 6 hydrates, 0.025 weight % of calcium chloride dihydrate, 0.085 weight % of ammonium dihydrogen phosphate, 0.0 15 weight % of diammonium hydrogen phosphate, and 99.425 weight % of deionized water) at 25±2° C.,
(b) the load applied to the measurement sample during the absorption is 50 g/cm$^2$ (4.83 kPa),
(c) the amount of the water-absorbent resin as a measurement sample is 0.055±0.005 g, and
(d) the water-absorbent resin as a measurement sample is uniformly spread on the wire net made of stainless steel attached to the bottom of the cylinder having an internal diameter of 60 mm,
wherein the absorption capacity without a load is measured with a sample drained with a centrifuge after immersed into an aqueous sodium chloride solution of 0.9 weight % for 30 minutes.

6. A water-absorbent resin according to claim 5, having a particle size distribution such that the ratio of parties having particle diameters of 600 to 300 μm is in the range of 65 to 85 weight %, and the ratio of particles having particle diameters of 300 to 150 μm is in the range of 10 to 30 weight %, where the particle size distribution is measured by a classification using a sieve.

7. A water-absorbent resin according to claim 5, having an L value of light index measured with a spectrophotometer of not less than 85, and the a value representing chromaticness index of in the range of −2 to 2 and the b value representing chromaticness index of in the range of 0 to 9.

8. A water-absorbent resin according to claim 5, wherein
time variation of single-layer absorption capacity of particles having particle diameters of 600 to 300 μm under a load is not less than 0.80,
time variation of single-layer absorption capacity of particles having particle diameters of 300 to 150 μm under a load is not less than 0.90,
variation between particles of the single-layer absorption capacity (10 min.) under a load is in the range of 0.90 to 1.10,
variation between particles of the single-layer absorption capacity (60 min.) under a load is not less than 0.90.

9. A sanitary material, comprising a water-absorbent resin and a fiber material,
wherein the water-absorbent resin is according to claim 5, and has a particle size distribution such that the ratio of particles having particles diameters of 600 to 300 μm is in the range of 65 to 85 weight %, and the ratio of particles having particle diameters of 300 to 150 μm is in the range of 10 to 30 weight %.

* * * * *